(12) United States Patent
Hatakeyama et al.

(10) Patent No.: US 10,303,056 B2
(45) Date of Patent: May 28, 2019

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Koji Hasegawa, Joetsu (JP); Masayoshi Sagehashi, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

(21) Appl. No.: 15/585,531

(22) Filed: May 3, 2017

(65) Prior Publication Data

US 2018/0004087 A1 Jan. 4, 2018

(30) Foreign Application Priority Data

Jun. 29, 2016 (JP) ................................. 2016-128886

(51) Int. Cl.
| | | |
|---|---|---|
| G03F 7/039 | (2006.01) | |
| G03F 7/16 | (2006.01) | |
| G03F 7/20 | (2006.01) | |
| G03F 7/38 | (2006.01) | |
| G03F 7/32 | (2006.01) | |
| C07D 317/04 | (2006.01) | |
| C07D 317/02 | (2006.01) | |
| G03F 7/004 | (2006.01) | |

(52) U.S. Cl.
CPC ......... *G03F 7/0392* (2013.01); *C07D 317/02* (2013.01); *C07D 317/04* (2013.01); *G03F 7/0045* (2013.01); *G03F 7/0046* (2013.01); *G03F 7/162* (2013.01); *G03F 7/168* (2013.01); *G03F 7/2004* (2013.01); *G03F 7/322* (2013.01); *G03F 7/38* (2013.01)

(58) Field of Classification Search
None
See application file for complete search history.

(56) References Cited

U.S. PATENT DOCUMENTS

| | | | | |
|---|---|---|---|---|
| 4,318,976 A | * | 3/1982 | Shu | G03F 7/0388 427/504 |
| 6,495,305 B1 | * | 12/2002 | Enomoto | G03F 7/091 430/270.1 |
| 7,482,108 B2 | | 1/2009 | Matsumaru et al. | |
| 8,475,999 B2 | * | 7/2013 | Masuyama | C07C 271/22 430/270.1 |
| 8,652,712 B2 | * | 2/2014 | Glodde | C07C 25/18 430/18 |
| 9,618,848 B2 | * | 4/2017 | Carcasi | H01L 21/0271 |
| 2006/0008736 A1 | * | 1/2006 | Kanda | G03F 7/0045 430/270.1 |
| 2007/0190459 A1 | * | 8/2007 | Hashimoto | G03F 7/11 430/270.1 |
| 2012/0202155 A1 | * | 8/2012 | Yao | C09D 161/24 430/311 |
| 2014/0080055 A1 | * | 3/2014 | Hatakeyama | G03F 7/038 430/270.1 |
| 2014/0356787 A1 | * | 12/2014 | Komuro | C07C 381/12 430/281.1 |

FOREIGN PATENT DOCUMENTS

| | | | |
|---|---|---|---|
| JP | 58-216243 | * | 12/1983 |
| JP | 61-156123 | * | 7/1986 |
| JP | 2006-45311 A | | 2/2006 |
| JP | 2006-178317 A | | 7/2006 |
| JP | 2015-161823 A | | 9/2015 |

OTHER PUBLICATIONS

Ueno et al. "Resist materials utilizing oxygen plasma resistance of iodine compounds", J. Electrochem. Soc.: Solid. State Sci. Tech., vol. 132(5) pp. 1168-1171 (May 1985).*
Taylor "X-ray resist trends", Sol. Stat. Technol., vol. 27(6) pp. 124-131 (Jun. 1984).*
Kishikawa et al., "Assessment of trade-off between resist resolution and sensitivity for optimization of hyper-NA immersion lithography", Proc. of SPIE (2007), vol. 6520, 65203L-1, Cited in specification. (9 pages).
Hutchinson., "The Shot Noise Impact on Resist Roughness in EUV Lithography", SPIE (1998),vol. 3331, pp. 531, Cited in specification. (7 pages).
Brainard et al., "Shot Noise, LER and Quantum Efficiency of EUV Photoresists", SPIE (2004), vol. 5374, pp. 74, Cited in specification. (12 pages).
Kozawa et al., "Basic aspects of acid generation processes in chemically amplified resists for electron beam lithography", SPIE (2005), vol. 5753, pp. 361, Cited in specification. (7 pages).
Nakano et al., "Deprotonation mechanism of poly (4-hydroxystyrene) and its derivative", SPIE (2005), vol. 5753, pp. 1034, Cited in specification. (6 pages).
Wang et al., "Novel Anionic Photoacid Generator (PAGs) and Photoresist for sub-50 nm Patterning by EUVL and EBL", SPIE (2007), vol. 6519, pp. 6519F1-1, Cited in specification. (6 pages).

* cited by examiner

*Primary Examiner* — Martin J Angebranndt
(74) *Attorney, Agent, or Firm* — Westerman, Hattori, Daniels & Adrian, LLP

(57) ABSTRACT

A positive resist composition based on a polymer comprising recurring units (a) of (meth)acrylate having an iodized lactone ring, and recurring units (b1) having a carboxyl group substituted with an acid labile group and/or recurring units (b2) having a phenolic hydroxyl group substituted with an acid labile group has a high sensitivity and resolution, and forms a pattern of good profile and minimal edge roughness after exposure.

2 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2016-128886 filed in Japan on Jun. 29, 2016, the entire contents of which are hereby incorporated by reference.

TECHNICAL FIELD

This invention relates to a positive resist composition, and more particularly to a chemically amplified positive resist composition; and a patterning process using the same.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, extreme ultraviolet (EUV) lithography of wavelength 13.5 nm, and double patterning version of the ArF lithography, on which active research efforts have been made.

As the feature size reduces, image blurs due to acid diffusion become a problem. To insure resolution for fine patterns with a size of 45 nm or less, not only an improvement in dissolution contrast is important as previously reported, but control of acid diffusion is also important as reported in Non-Patent Document 1. Since chemically amplified resist compositions are designed such that sensitivity and contrast are enhanced by acid diffusion, an attempt to minimize acid diffusion by reducing the temperature and/or time of post-exposure bake (PEB) fails, resulting in drastic reductions of sensitivity and contrast.

A triangular tradeoff relationship among sensitivity, resolution, and edge roughness has been pointed out. Specifically, acid diffusion must be suppressed to achieve a resolution improvement whereas a short acid diffusion distance leads to a loss of sensitivity.

The addition of an acid generator capable of generating a bulky acid is an effective means for suppressing acid diffusion. It was then proposed to incorporate recurring units derived from an onium salt having a polymerizable unsaturated bond in a polymer as acid generator. Patent Document 1 discloses a sulfonium salt having a polymerizable unsaturated bond capable of generating a specific sulfonic acid and a similar iodonium salt. Patent Document 2 discloses a sulfonium salt having sulfonic acid directly attached to the main chain.

A tradeoff relationship between sensitivity and edge roughness has been pointed out. For example, Non-Patent Document 2 describes that sensitivity is in inverse proportion to edge roughness. It is expected that the edge roughness of a resist film is reduced by increasing the exposure dose to reduce shot noise. Non-Patent Document 3 describes a tradeoff between sensitivity and roughness in the EUV lithography in that a resist material containing a more amount of quencher is effective in reducing roughness, but suffers from a decline of sensitivity at the same time. There is a need to enhance the quantum efficiency of acid generation in order to overcome the problem.

With respect to the acid generating mechanism triggered by EB exposure, Non-Patent Document 4 reports that PAG releases acid through the mechanism that a polymer is excited by exposure so that electrons migrate to the PAG. Since the irradiation energy of EB or EUV is higher than the threshold value (10 eV) of ionization potential energy of a base polymer, it is presumed that the base polymer is readily ionized. An exemplary material of accelerating electron migration is hydroxystyrene.

It is reported in Non-Patent Document 5 that poly-4-hydroxystyrene has a higher acid generation efficiency in EB exposure than poly-4-methoxystyrene, indicating that poly-4-hydroxystyrene provides for efficient migration of electrons to PAG upon EB exposure.

Non-Patent Document 6 proposes a material obtained through copolymerization of hydroxystyrene for increasing the acid generation efficiency by electron migration, a methacrylate of PAG having sulfonic acid directly bonded to a polymer backbone for suppressing acid diffusion, and a methacrylate having an acid labile group.

Since hydroxystyrene has a phenolic hydroxyl group which is weakly acidic, it is effective for reducing swell in alkaline developer, but causes to increase acid diffusion. On the other hand, a methacrylate having lactone ring as the adhesive group is widely employed in the ArF resist composition. Since this methacrylate has high hydrophilicity and no alkaline solubility, it is ineffective for reducing swell, but effective for suppressing acid diffusion. A combination of hydroxystyrene and lactone ring-bearing methacrylate as the adhesive group can establish a fairly good balance among sensitivity improvement, swell reduction, and acid diffusion control, but is still insufficient.

Copolymerization of hydroxyphenyl methacrylate with lactone ring-bearing methacrylate and optionally methacrylate of PAG having sulfonic acid directly bonded to the polymer backbone is effective for forming resist compositions having a high sensitivity, high resolution, and controlled acid diffusion. An attempt to increase the content of hydroxyphenyl methacrylate is effective for further increasing the sensitivity. However, as the content of hydroxyphenyl methacrylate increases, alkaline solubility increases, indicating that the pattern will undergo a film thickness loss and eventually collapse.

Since iodine is highly absorptive at wavelength 13.5 nm, it generates secondary electrons upon exposure to which the acid generator is sensitive, indicating a higher sensitivity. For example, iodonium salts have a higher sensitivity than sulfonium salts. Patent Document 3 shows an iodized polymer, specifically a polymer comprising recurring units having an iodized aromatic group. Since the aromatic group is electron absorptive, 25 secondary electrons generated by iodine are taken into the aromatic group, leading to a low sensitizing effect. To develop a resist composition having higher sensitivity and resolution, a substance capable of efficiently exerting a sensitizing effect is desired.

CITATION LIST

Patent Document 1: JP-A 2006-045311 (U.S. Pat. No. 7,482,108)
Patent Document 2: JP-A 2006-178317
Patent Document 3: JP-A 2015-161823
Non-Patent Document 1: SPIE Vol. 6520, 65203L-1 (2007)
Non-Patent Document 2: SPIE Vol. 3331, p 531 (1998)
Non-Patent Document 3: SPIE Vol. 5374, p 74 (2004)
Non-Patent Document 4: SPIE Vol. 5753, p 361 (2005)
Non-Patent Document 5: SPIE Vol. 5753, p 1034 (2005)
Non-Patent Document 6: SPIE Vol. 6519, p 6519F1-1 (2007)

SUMMARY OF INVENTION

An object of the present invention is to provide a positive resist composition comprising a specific polymer, which composition exhibits a higher sensitivity and resolution than the prior art positive resist compositions and minimal edge roughness (LER, LWR), and forms a pattern of good profile after exposure; and a patterning process using the resist composition.

Making extensive investigations in search for a positive resist material capable of meeting the current requirements including high sensitivity, high resolution, and minimal edge roughness, the inventors have found that a polymer comprising recurring units derived from (meth)acrylate having an iodized lactone ring is quite effective as a base resin in a positive resist composition.

The inventors have found that a polymer comprising recurring units derived from (meth)acrylate having an iodized lactone ring and recurring units having a carboxyl or phenolic hydroxyl group whose hydrogen is substituted by an acid labile group is used as a base resin in a positive resist composition for the purpose of improving dissolution contrast, and that the positive resist composition comprising the polymer is improved in such properties as sensitivity, a contrast of alkali dissolution rate before and after exposure, acid diffusion suppressing effect, resolution, and profile and edge roughness of a pattern after exposure, and thus best suited as a micropatterning material for the fabrication of VLSI and photomasks.

In one aspect, the invention provides a positive resist composition comprising a base resin containing a polymer comprising recurring units (a) having the formula (a), and recurring units (b1) having a carboxyl group whose hydrogen is substituted by an acid labile group and/or recurring units (b2) having a phenolic hydroxyl group whose hydrogen is substituted by an acid labile group, the polymer having a weight average molecular weight of 1,000 to 500,000.

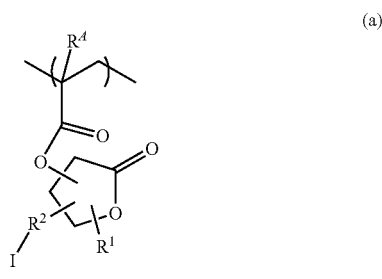

(a)

Herein $R^A$ is hydrogen or methyl, $R^1$ is hydrogen or $C_1$-$C_4$ straight or branched alkyl, and $R^2$ is a single bond or methylene.

In a preferred embodiment, the recurring units (b1) and the recurring units (b2) have the formulae (b1) and (b2), respectively.

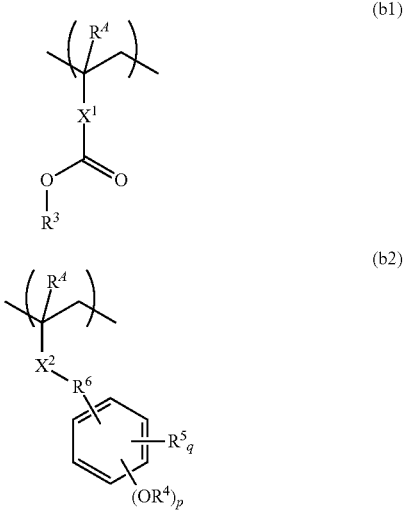

Herein $R^A$ is as defined above, $R^3$ and $R^4$ each are an acid labile group, $R^5$ is hydrogen, fluorine, trifluoromethyl, cyano, or $C_1$-$C_6$ straight, branched or cyclic alkyl, $R^6$ is a single bond or $C_1$-$C_6$ straight or branched alkylene group in which at least one carbon atom may be substituted by an ether or ester moiety, p is 1 or 2, q is an integer of 0 to 4, $X^1$ is a single bond, $C_1$-$C_{14}$ linking group containing an ester, ether moiety or lactone ring, phenylene group or naphthylene group, and $X^2$ is a single bond, —C(=O)—O— or —C(=O)—NH—.

In a preferred embodiment, the polymer further comprises recurring units (c) having an adhesive group which is selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is —S— or —NH—.

In a preferred embodiment, the polymer further comprises recurring units of at least one type selected from recurring units having the formulae (d1), (d2) and (d3).

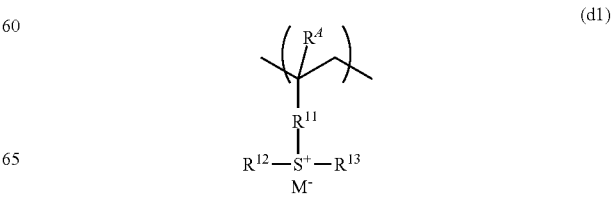

(d1)

(d2)

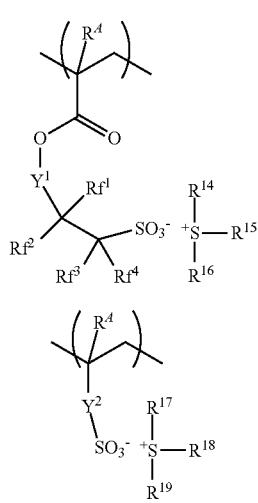

(d3)

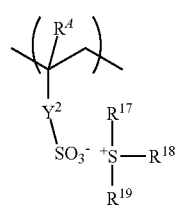

Herein $R^A$ is each independently hydrogen or methyl, $R^{11}$ is a single bond, phenylene group, —O—$R^2$—, or —C(=O)—$Z^1$13 $R^{21}$—, $Z^1$ is —O— or —NH—, $R^{21}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety, $Rf^1$ to $Rf^4$ are each independently fluorine, hydrogen or trifluoromethyl, at least one of $Rf^1$ to $Rf^4$ being fluorine, $R^{12}$ to $R^{19}$ are each independently a $C_1$-$C_{12}$ straight, branched or cyclic alkyl group which may contain a carbonyl, ester or ether moiety, $C_6$-$C_{12}$ aryl group, $C_7$-$C_{20}$ aralkyl group, or mercaptophenyl group, $Y^1$ is a single bond or a $C_1$-$C_{12}$ linking group which may contain an ester, ether moiety or lactone ring, $Y^2$ is a single bond, methylene, ethylene, phenylene, fluorinated phenylene, —O—$R^{22}$—, or —C(=O)—$Z^2$—$R^{22}$—, $Z^2$ is —O— or —NH—, $R^{22}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety, and $M^-$ is a non-nucleophilic counter ion.

The resist composition may further comprise an organic solvent and an acid generator, the composition being a chemically amplified positive resist composition. The resist composition may further comprise a basic compound and/or a surfactant.

In another aspect, the invention provides a pattern forming process comprising the steps of coating the positive resist composition defined above onto a substrate, baking to form a resist film, exposing the resist film to high-energy radiation, and developing the exposed resist film in a developer.

Typically, the high-energy radiation is I-line, KrF excimer laser, ArF excimer laser, EB, or EUV of wavelength 3 to 15 nm.

Advantageous Effects of Invention

The positive resist composition has a high sensitivity due to the enhanced decomposition efficiency of acid generator, a satisfactory effect of suppressing acid diffusion, and a high resolution, lends itself to the lithography process, and forms a pattern of good profile and minimal edge roughness after exposure. Because of these advantages, the composition is readily implemented in practice and best suited as a micro-patterning material for photomasks by EB lithography or for VLSIs by i-line, KrF excimer laser, ArF excimer laser, EB or EUV lithography.

DESCRIPTION OF EMBODIMENTS

As used herein, the singular forms "a," "an" and "the" include plural referents unless the context clearly dictates otherwise. The notation (Cn-Cm) means a group containing from n to m carbon atoms per group. As used herein, the term "iodized" group means an iodine-containing group. In chemical formulae, Me stands for methyl and Ac for acetyl.

The acronym "PAG" stands for photoacid generator, "PEB" for post-exposure bake, "LER" for line edge roughness, "LWR" for line width roughness, "EUV" for extreme ultraviolet, and "EB" for electron beam.

One embodiment of the invention is a positive resist composition comprising a base resin containing a polymer comprising recurring units (a) having the formula (a), and recurring units (b1) having a carboxyl group whose hydrogen is substituted by an acid labile group and/or recurring units (b2) having a phenolic hydroxyl group whose hydrogen is substituted by an acid labile group.

(a)

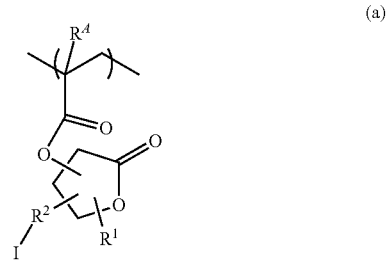

Herein $R^A$ is hydrogen or methyl, $R^1$ is hydrogen or a $C_1$-$C_4$ straight or branched alkyl group, and $R^2$ is a single bond or methylene.

The recurring units (a) are derived from a (meth)acrylate having an iodized lactone ring. Since iodine atom is highly absorptive to EUV, it generates secondary electrons upon EUV exposure. The energy is transferred from the electrons to the acid generator to generate an acid. The significant sensitizing effect of (meth)acrylate having an iodized lactone ring ensures to formulate a resist composition having a high sensitivity. At the same time, the iodized lactone ring is highly effective for adhesion and acid diffusion suppression, enabling to form a resist pattern with an improved resolution, CD uniformity and edge roughness.

The recurring units (a) are derived from a monomer Ma having the following formula (Ma), (Ma)

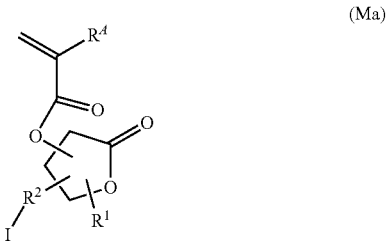

Herein $R^A$, $R^1$ and $R^2$ are as defined above.

The monomer Ma may be synthesized by reacting (meth)acrylic acid with an iodized hydroxylactone to form a (meth)acrylate. Examples of the monomer Ma are shown below, but not limited thereto. Herein $R^4$ is as defined above.

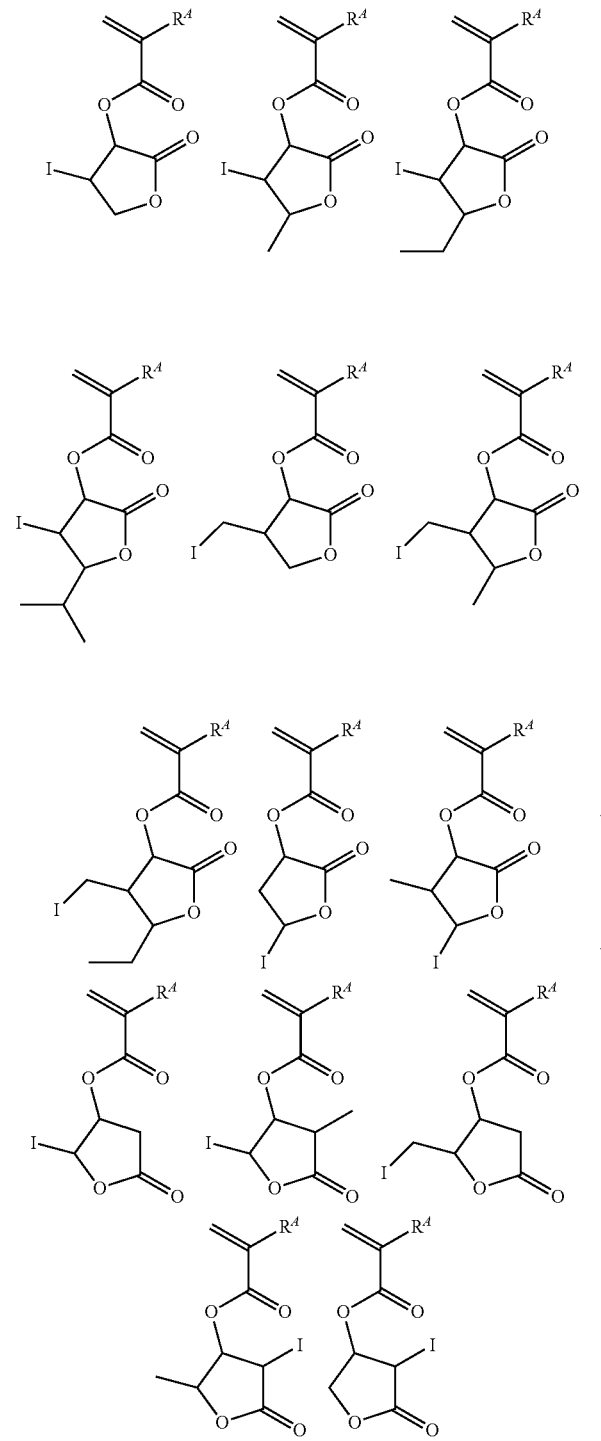

Preferably the recurring units (b1) and (b2) have the formulae (b1) and (b2), respectively.

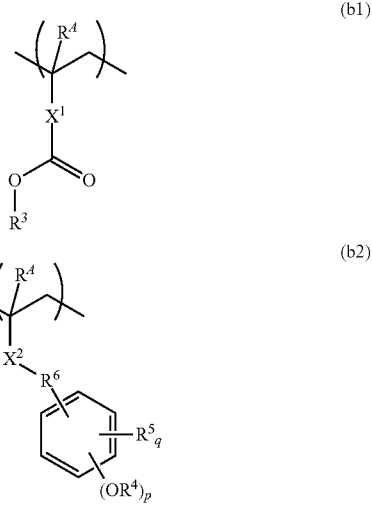

Herein $R^4$ is as defined above. $R^3$ and $R^4$ each are an acid labile group. $R^5$ is hydrogen, fluorine, trifluoromethyl, cyano, or a $C_1$-$C_6$ straight, branched or cyclic alkyl group. $R^6$ is a single bond or a $C_1$-$C_6$ straight or branched alkylene group in which at least one carbon atom may be substituted by an ether or ester moiety, p is 1 or 2, and q is an integer of 0 to 4. $X^1$ is a single bond, a $C_1$-$C_{14}$ linking group which contains an ester, ether moiety or lactone ring, a phenylene group or a naphthylene group. $X^2$ is a single bond, —C(=O)—O— or —C(=O)—NH—.

Monomers Mb1 and Mb2 from which the recurring units (b1) and (b2) are derived are represented by the formulae (Mb1) and (Mb2), respectively.

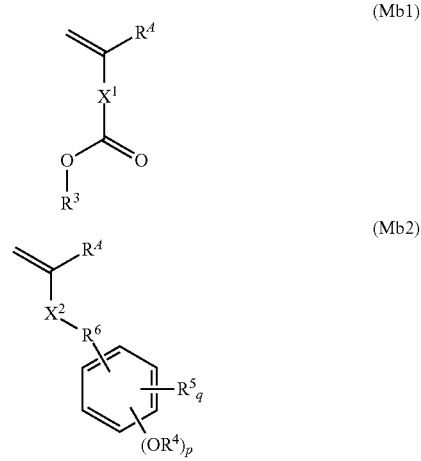

Herein $R^4$, $R^3$ to $R^6$, $X^1$, $X^2$, p and q are as defined above.

Examples of the monomer Mb1 are given below, but not limited thereto. Herein $R^4$ and $R^3$ are as defined above.

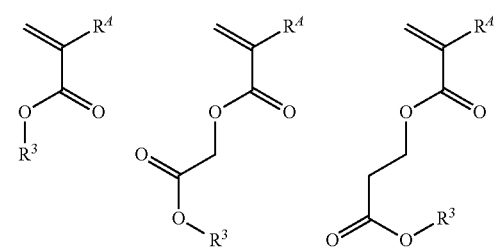
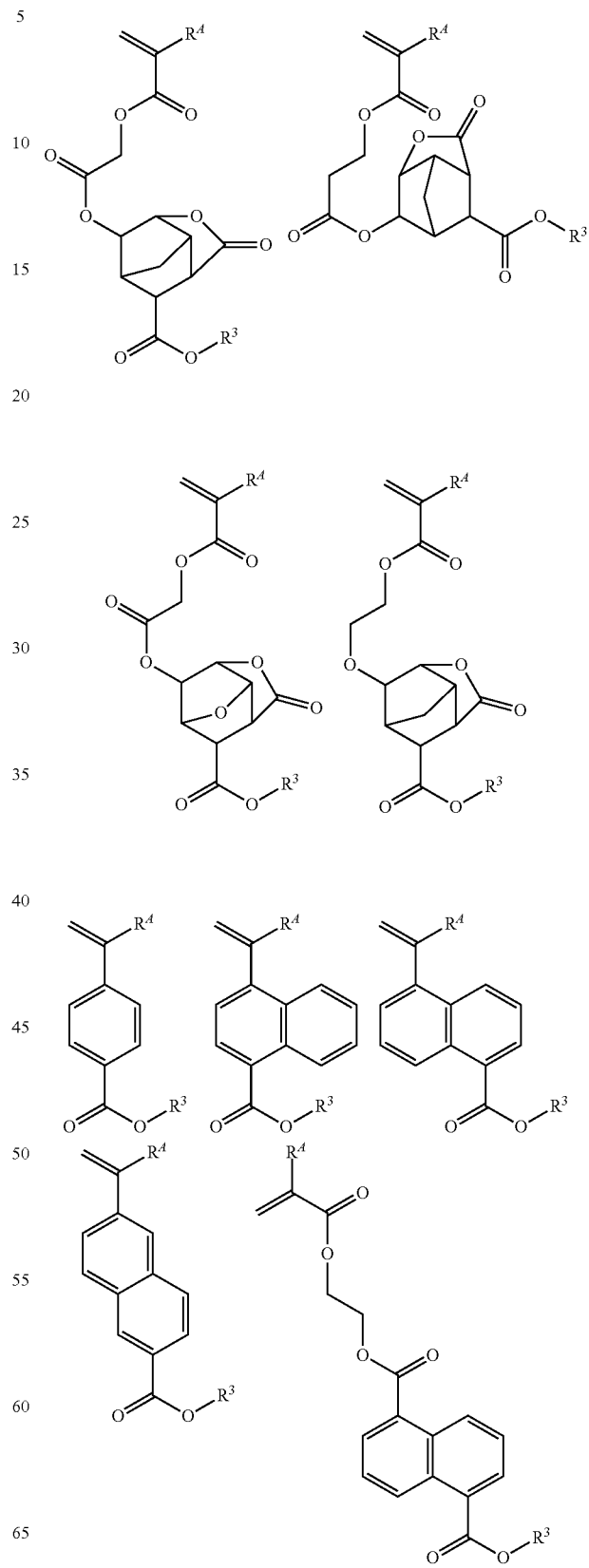

-continued
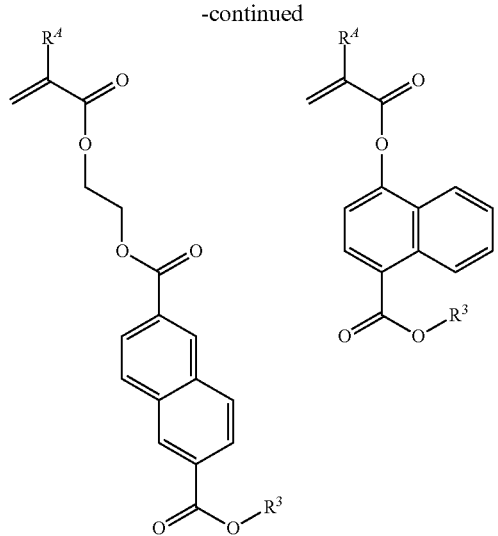
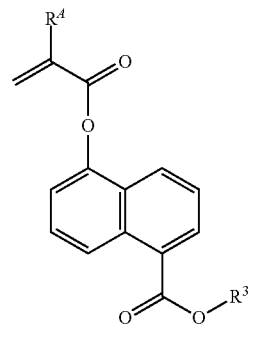
Examples of the monomer Mb2 are given below, but not limited thereto. Herein $R^A$ and $R^B$ are as defined above.
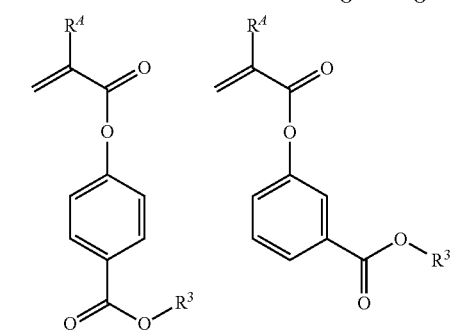
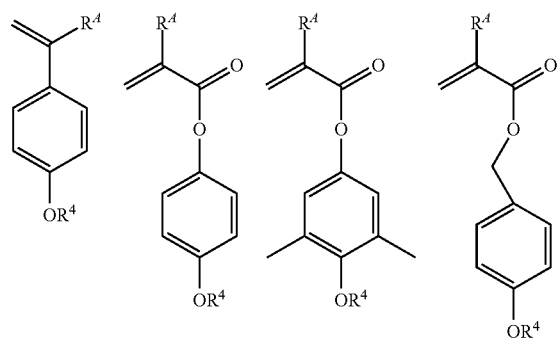
The acid labile groups represented by $R^3$ and $R^4$ may be selected from a variety of such groups. The acid labile groups may be the same or different and preferably include groups of the following formulae (A-1) to (A-3).
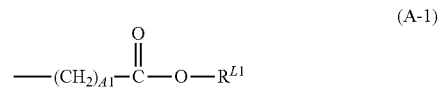
(A-1)

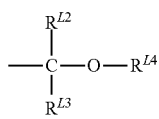
(A-2)

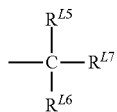
(A-3)

In formula (A-1), $R^{L1}$ is a $C_4$-$C_{20}$, preferably $C_4$-$C_{15}$ tertiary alkyl group, a trialkylsilyl group in which each alkyl moiety has 1 to 6 carbon atoms, a $C_4$-$C_{20}$ oxoalkyl group, or a group of formula (A-3). Letter A1 is an integer of 0 to 6.

Exemplary tertiary alkyl groups are tert-butyl, tert-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

Examples of the acid labile group of formula (A-1) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Also included are acid labile groups having the formulae (A-1)-1 to (A-1)-10.

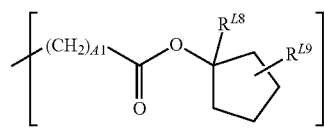
(A-1)-1

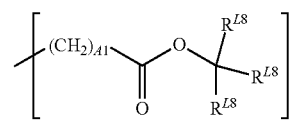
(A-1)-2

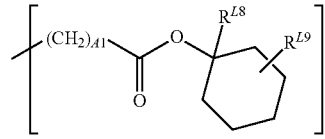
(A-1)-3

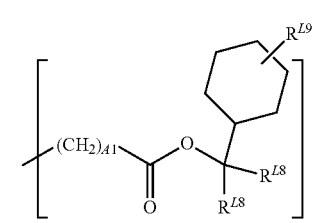
(A-1)-4

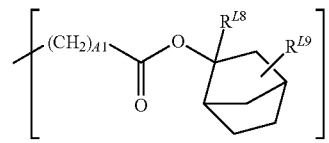
(A-1)-5

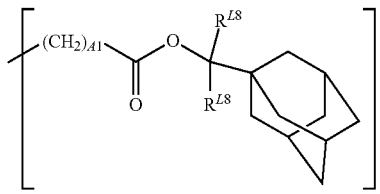
(A-1)-6

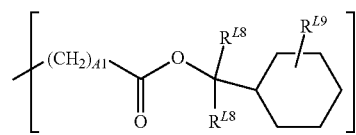
(A-1)-7

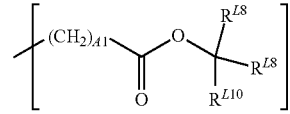
(A-1)-8

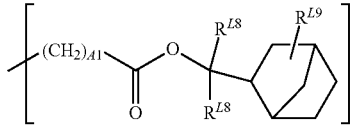
(A-1)-9

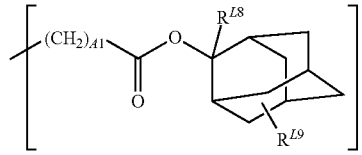
(A-1)-10

Herein $R^{L8}$ is each independently a $C_1$-$C_{10}$ straight, branched or cyclic alkyl group or $C_6$-$C_{20}$ aryl group. $R^{L9}$ is hydrogen or a $C_1$-$C_{10}$ straight, branched or cyclic alkyl group. $R^{L10}$ is each independently a $C_2$-$C_{10}$ straight, branched or cyclic alkyl group or $C_6$-$C_{20}$ aryl group, and A1 is as defined above.

In formula (A-2), $R^{L2}$ and $R^{L3}$ are each independently hydrogen or a $C_1$-$C_{18}$, preferably $C_1$-$C_{10}$ straight, branched or cyclic alkyl group. Exemplary alkyl groups include methyl, ethyl, propyl, isopropyl, n-butyl, sec-butyl, tert-butyl, cyclopentyl, cyclohexyl, 2-ethylhexyl, and n-octyl. $R^{L4}$ is a $C_1$-$C_{18}$, preferably $C_1$-$C_{10}$ monovalent hydrocarbon group which may contain a heteroatom such as oxygen, examples of which include straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

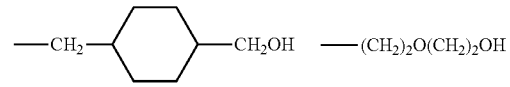

-continued

—(CH$_2$)$_6$OH 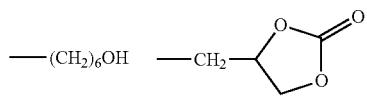

A pair of R$^{L2}$ and R$^{L3}$, R$^{L2}$ and R$^{L4}$, or R$^{L3}$ and R$^{L4}$ may bond together to form a ring with the carbon or the carbon and oxygen atoms to which they are attached. The ring-forming pair of R$^{L2}$, R$^{L3}$ and R$^{L4}$ is a C$_1$-C$_{18}$, preferably C$_1$-C$_{10}$ straight or branched alkylene group, while the ring preferably has 3 to 10 carbon atoms, more preferably 4 to 10 carbon atoms.

Of the acid labile groups of formula (A-2), the straight and branched ones are exemplified by groups having the following formulae (A-2)-1 to (A-2)-69.

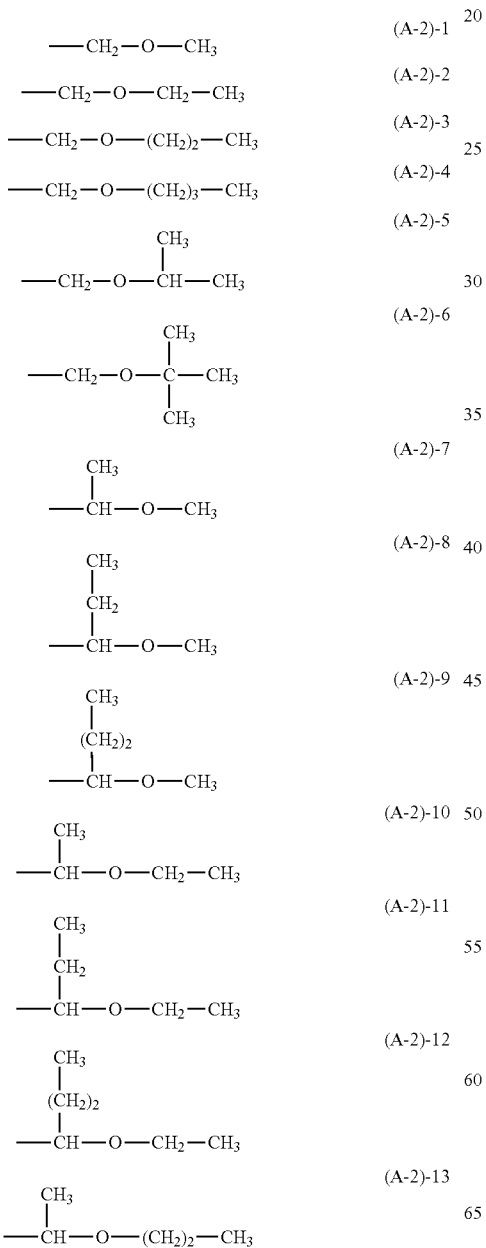

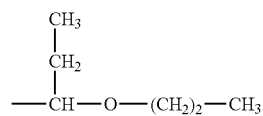
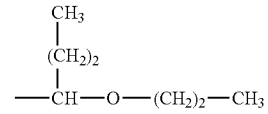
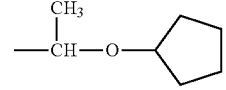
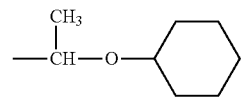
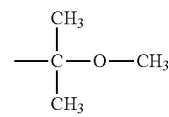
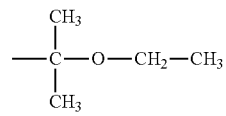
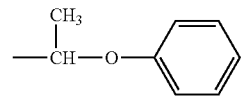
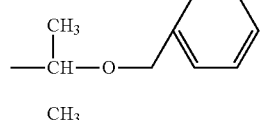
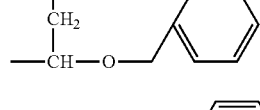
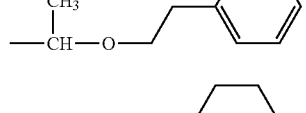
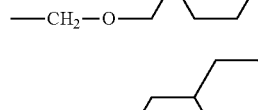
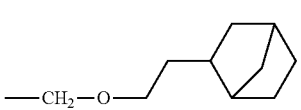

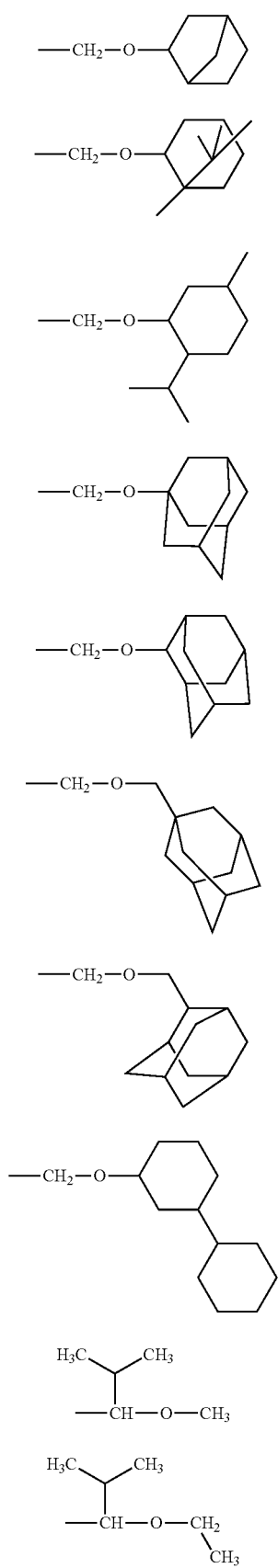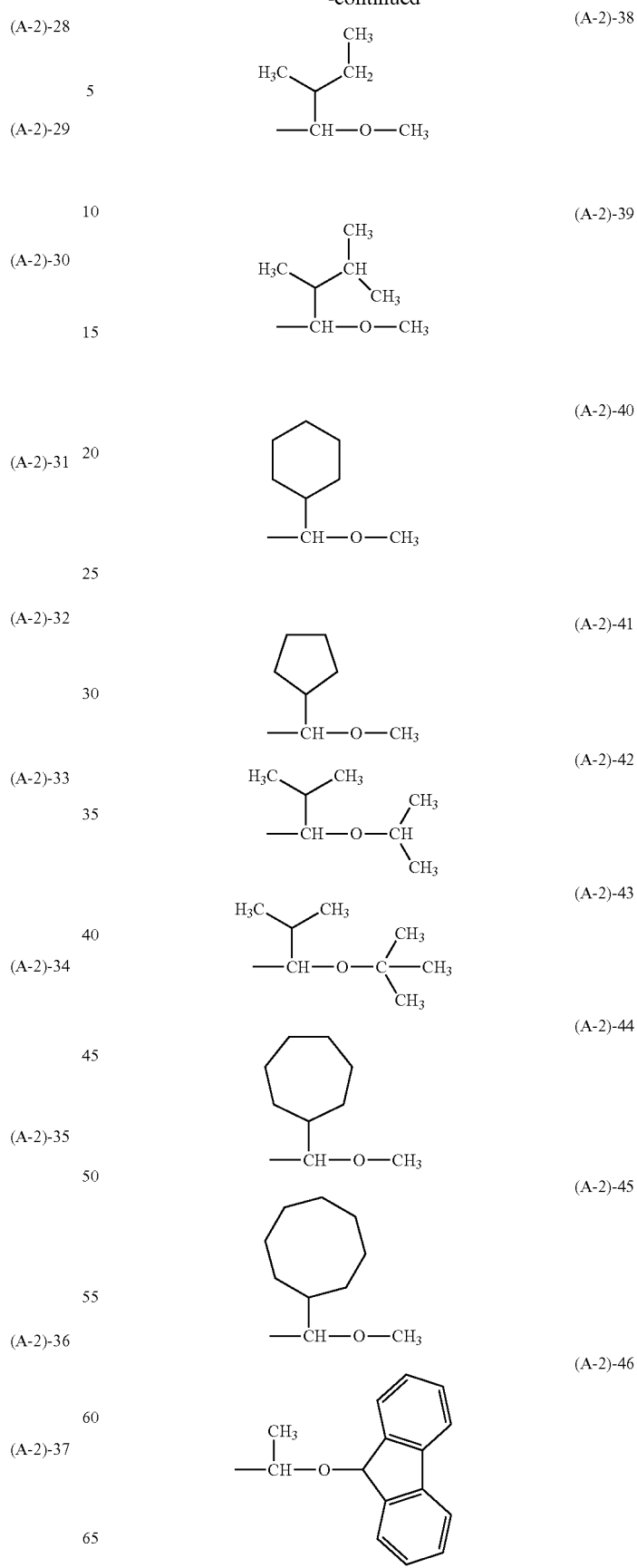

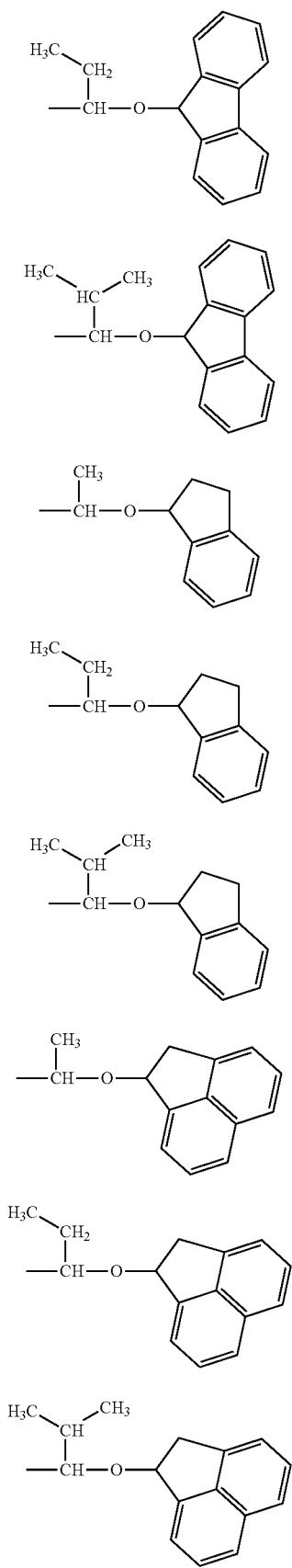
(A-2)-47
(A-2)-48
(A-2)-49
(A-2)-50
(A-2)-51
(A-2)-52
(A-2)-53
(A-2)-54
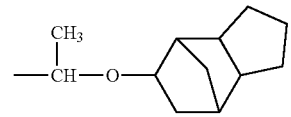 (A-2)-55
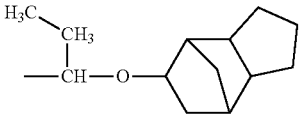 (A-2)-56
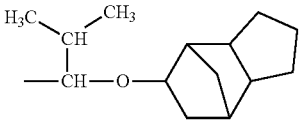 (A-2)-57
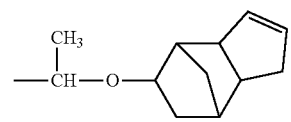 (A-2)-58
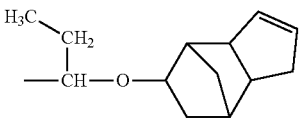 (A-2)-59
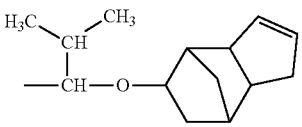 (A-2)-60
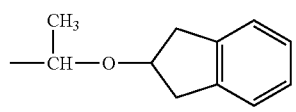 (A-2)-61
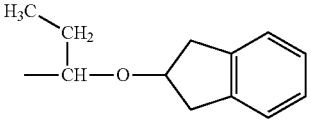 (A-2)-62
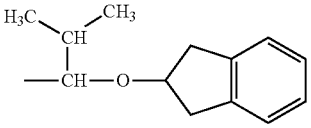 (A-2)-63
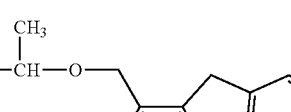 (A-2)-64
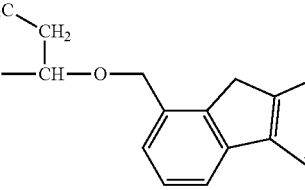 (A-2)-65

-continued

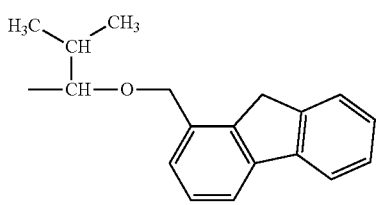
(A-2)-66

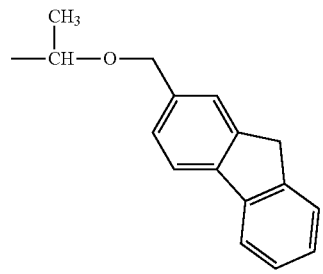
(A-2)-67

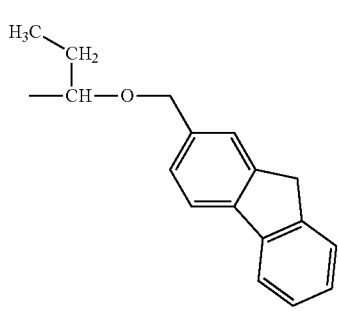
(A-2)-68

(A-2)-69

Of the acid labile groups of formula (A-2), the cyclic ones are, for example, tetrahydrofuran-2-yl, 2-methyltetrahydrofuran-2-yl, tetrahydropyran-2-yl, and 2-methyltetrahydropyran-2-yl.

Other examples of acid labile groups include those of the formula (A-2a) or (A-2b) while the polymer may be cross-linked within the molecule or between molecules with these acid labile groups.

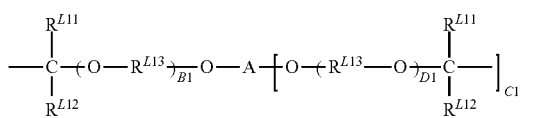
(A-2a)

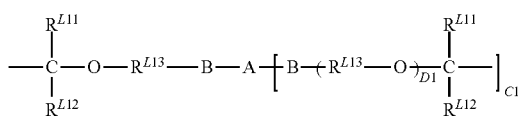
(A-2b)

Herein $R^{L11}$ and $R^{L12}$ each are hydrogen or a $C_1$-$C_8$ straight, branched or cyclic alkyl group, or $R^{L11}$ and $R^{L12}$, taken together, may form a ring with the carbon atom to which they are attached, and the ring-forming pair of $R^{L11}$ and $R^{L12}$ is a $C_1$-$C_8$ straight or branched alkylene group. $R^{L13}$ is a $C_1$-$C_{10}$ straight, branched or cyclic alkylene group. Each of B1 and D1 is an integer of 0 to 10, preferably 0 to 5, and C1 is an integer of 1 to 7, preferably 1 to 3.

"A" is a (C1+1)-valent aliphatic or alicyclic saturated hydrocarbon group, aromatic hydrocarbon group or heterocyclic group having 1 to 50 carbon atoms, which may be separated by a heteroatom or in which some carbon-bonded hydrogen atoms may be substituted by hydroxyl, carboxyl, acyl groups or fluorine atoms. Preferably, "A" is selected from $C_1$-$C_{20}$ straight, branched or cyclic alkylene, alkyltriyl and alkyltetrayl groups, and $C_6$-$C_{30}$ arylene groups. "B" is —CO—O—, —NHCO—O— or —NHCONH—.

The crosslinking acetal groups of formulae (A 2a) and (A-2b) are exemplified by the following formulae (A-2)-70 through (A-2)-77.

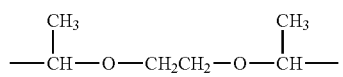
(A-2)-70

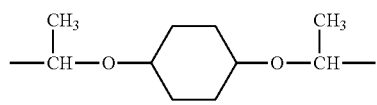
(A-2)-71

(A-2)72

(A-2)-73

-continued

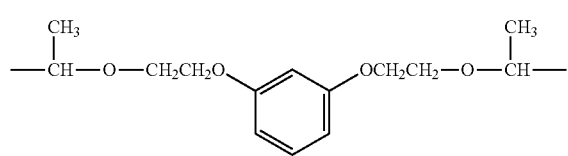
(A-2)-74

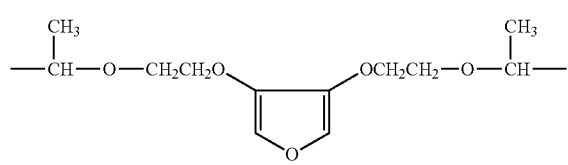
(A-2)-75

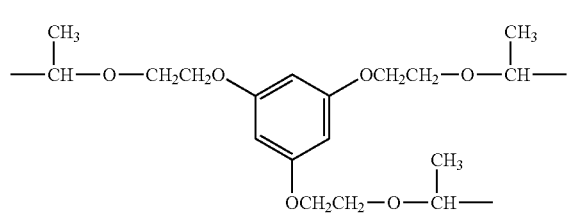
(A-2)-76

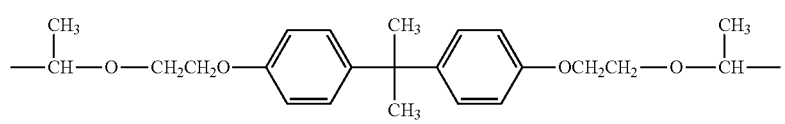
(A-2)-77

In formula (A-3), $R^{L5}$, $R^{L6}$ and $R^{L7}$ are each independently a monovalent hydrocarbon group, typically a $C_1$-$C_{20}$ straight, branched or cyclic alkyl group or $C_2$-$C_{20}$ straight, branched or cyclic alkenyl group, which may contain a heteroatom such as oxygen, sulfur, nitrogen or fluorine. A pair of $R^{L5}$ and $R^{L6}$, $R^{L5}$ and $R^{L7}$, or $R^{L6}$ and $R^{L7}$ may bond together to form a $C_3$-$C_{20}$ aliphatic ring with the carbon atom to which they are attached.

Exemplary groups of formula (A-3) include tert-butyl, triethylcarbyl, 1-ethylnorbornyl, 1-methylcyclohexyl, 1-ethylcyclopentyl, 2-(2-methyl)adamantyl, 2-(2-ethyl)adamantyl, and tert-pentyl.

Other exemplary groups of formula (A-3) include those of the k g formulae (A-3)-1 to (A-3)-18.

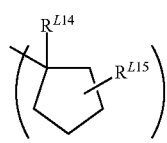
(A-3)-1

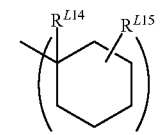
(A-3)-2

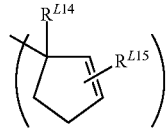
(A-3)-3

-continued

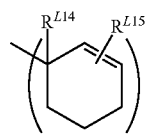
(A-3)-4

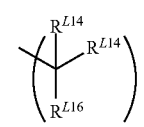
(A-3)-5

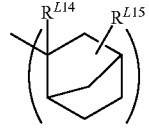
(A-3)-6

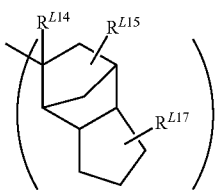
(A-3)-7

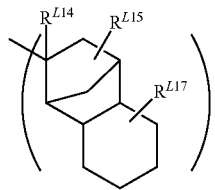
(A-3)-8

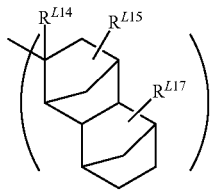 (A-3)-9

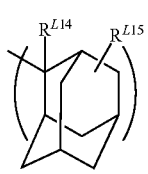 (A-3)-10

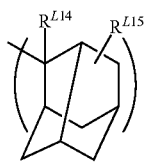 (A-3)-11

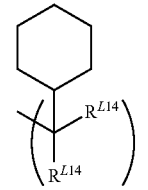 (A-3)-12

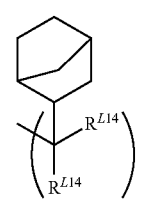 (A-3)-13

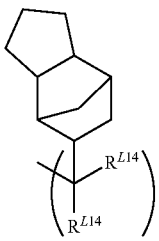 (A-3)-14

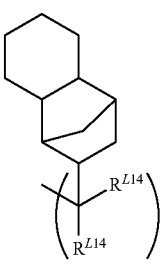 (A-3)-15

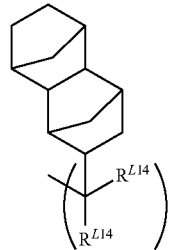 (A-3)-16

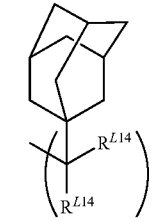 (A-3)-17

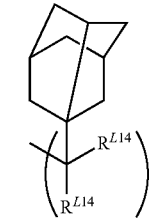 (A-3)-18

Herein $R^{L14}$ is each independently a $C_1$-$C_8$ straight, branched or cyclic alkyl group or $C_6$-$C_{20}$ aryl group, typically phenyl. $R^{L15}$ and $R^{L17}$ each are hydrogen or a $C_1$-$C_{20}$ straight, branched or cyclic alkyl group. $R^{L16}$ is a $C_6$-$C_{20}$ aryl group, typically phenyl.

Other acid labile groups include those of the formulae (A-3)-19 and (A-3)-20 while the polymer may be crosslinked within the molecule or between molecules with these acid labile groups.

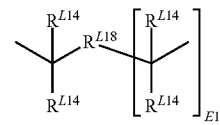 (A-3)-19

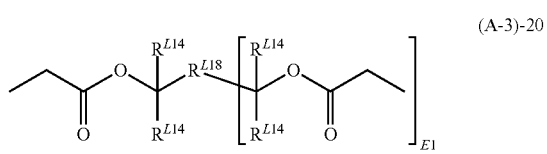 (A-3)-20

Herein $R^{L14}$ is as defined above. $R^{L18}$ is a (E1+1)-valent $C_1$-$C_{20}$ straight, branched or cyclic aliphatic hydrocarbon group or (E1+1)-valent $C_6$-$C_{20}$ aromatic hydrocarbon group, which may contain a heteroatom such as oxygen, sulfur or nitrogen, and E1 is an integer of 1 to 3.

Of recurring units having acid labile groups of formula (A-3), recurring units of (meth)acrylate having an exo-form structure represented by the formula (A-3)-21 are preferred.

(A-3)-21

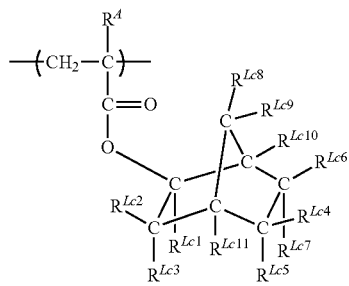

Herein $R^A$ is hydrogen or methyl. $R^{Lc1}$ is a $C_1$-$C_8$ straight, branched or cyclic alkyl group or an optionally substituted $C_6$-$C_{20}$ aryl group; $R^{Lc2}$ to $R^{Lc7}$, $R^{Lc10}$ and $R^{Lc11}$ are each independently hydrogen or a $C_1$-$C_{15}$ monovalent hydrocarbon group which may contain a heteroatom. $R^{Lc8}$ and $R^{Lc9}$ are hydrogen. Alternatively, a pair of $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$ and $R^{Lc9}$, or $R^{Lc9}$ and $R^{Lc10}$ may bond together to form a ring with the carbon atom to which they are attached, and the ring-forming pair is a $C_1$-$C_{15}$ divalent hydrocarbon group which may contain a heteroatom. Also, a pair of $R^{Lc2}$ and $R^{Lc11}$, $R^{Lc8}$ and $R^{Lc11}$, or $R^{Lc4}$ and $R^{Lc6}$ which are attached to vicinal carbon atoms may bond together directly to form a double bond. The formula also represents an enantiomer.

The monomers from which recurring units having formula (A-3)-21 are derived are described in U.S. Pat. No. 6,448,420 (JP-A 2000-327633). Illustrative non-limiting examples of suitable monomers are given below. Herein $R^A$ is as defined above.

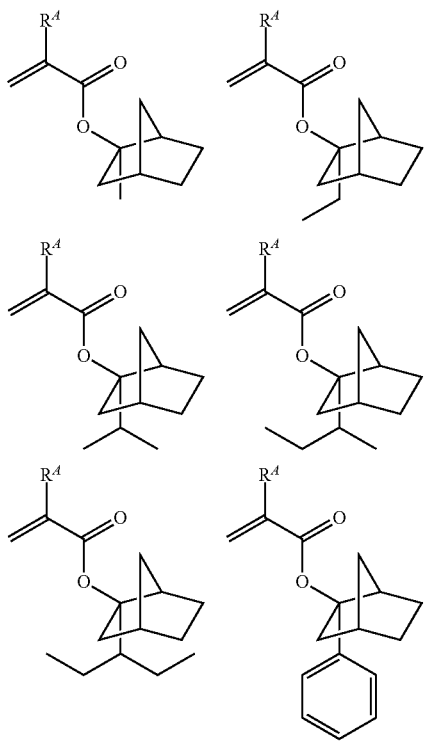

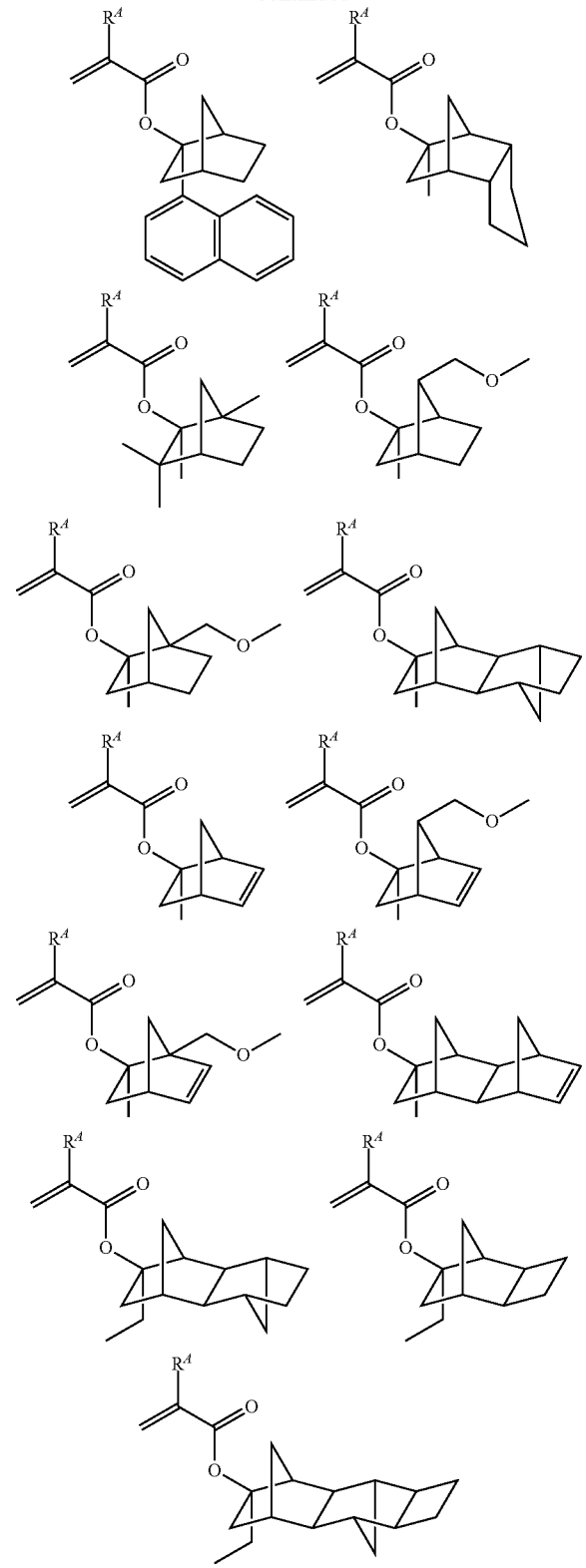

Also included in the recurring units having acid labile groups of formula (A-3) are those derived from (meth) acrylates containing furandiyl, tetrahydrofurandiyl or oxanorbornanediyl as represented by the following formula (A-3)-22.

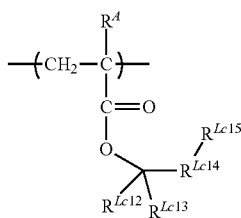

(A-3)-22

Herein $R^A$ is as defined above. $R^{Lc12}$ and $R^{Lc13}$ are each independently a $C_1$-$C_{10}$ straight, branched or cyclic monovalent hydrocarbon group, or $R^{Lc12}$ and $R^{Lc13}$ may bond together to form an aliphatic ring with the carbon atom to which they are attached. $R^{Lc14}$ is furandiyl, tetrahydrofurandiyl or oxanorbornanediyl, $R^{Lc15}$ is hydrogen or a $C_1$-$C_{10}$ straight, branched or cyclic monovalent hydrocarbon group which may contain a heteroatom.

Examples of the monomers from which the recurring units having formula (A-3)-22 are derived are shown below. Herein $R^A$ is as defined above.

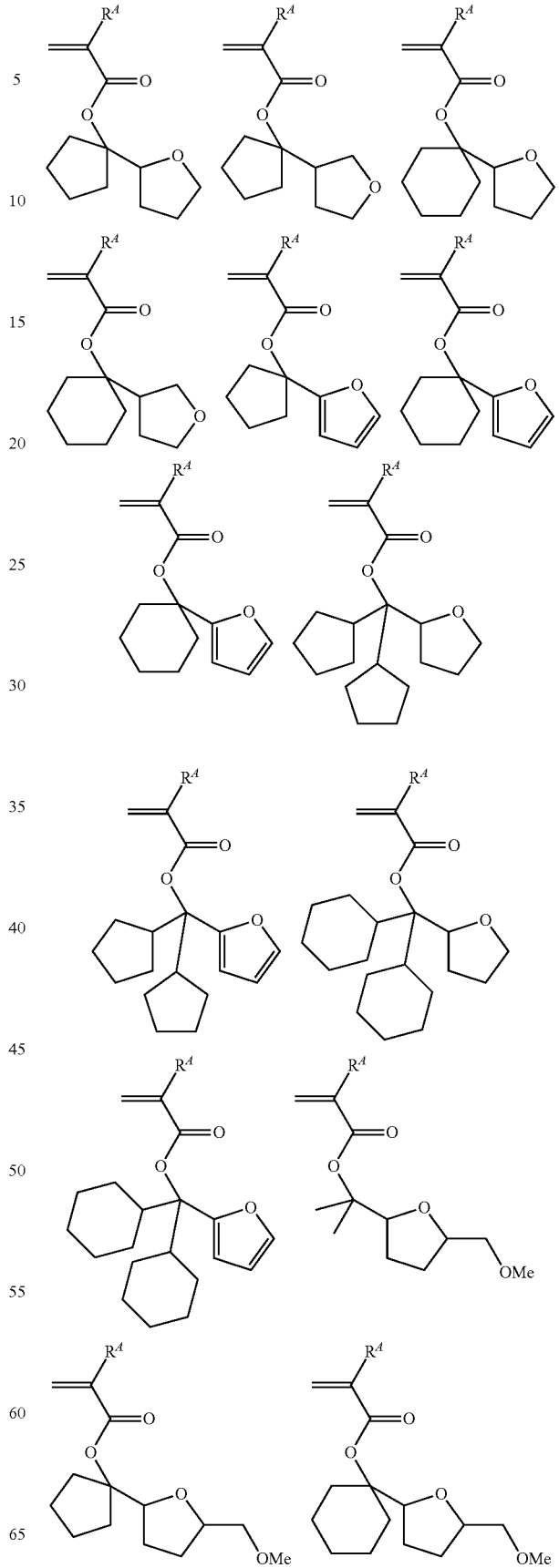

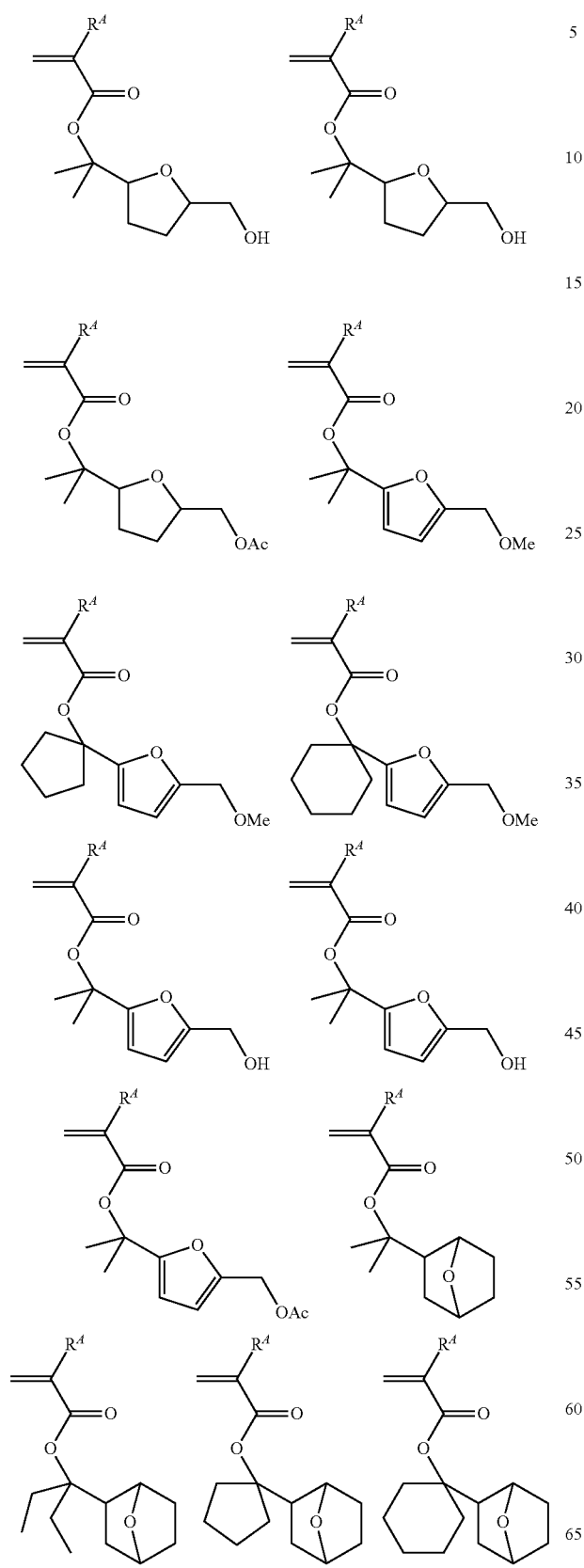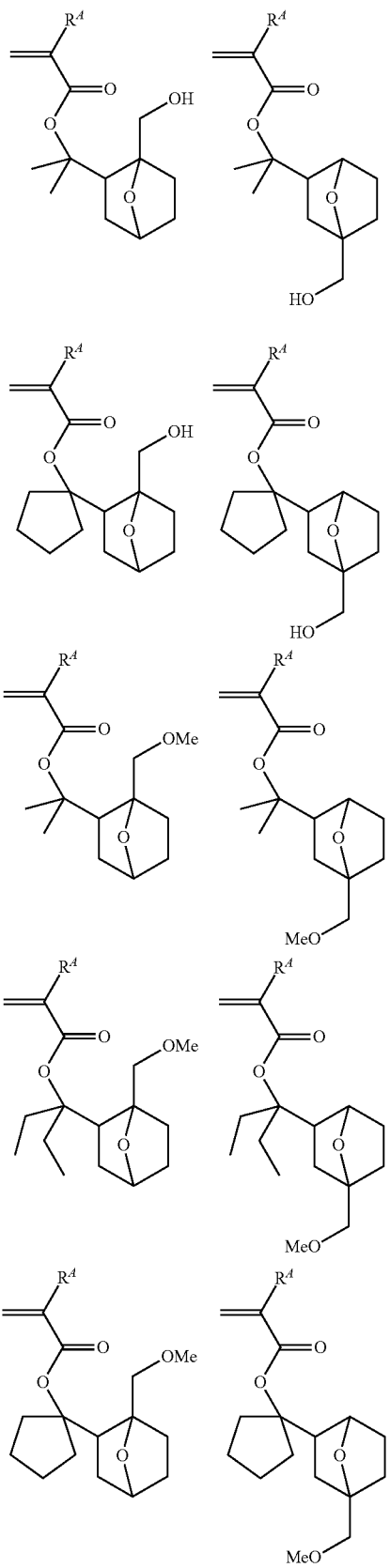

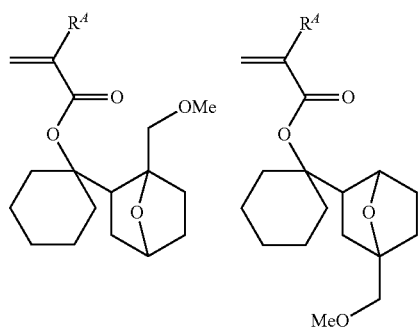

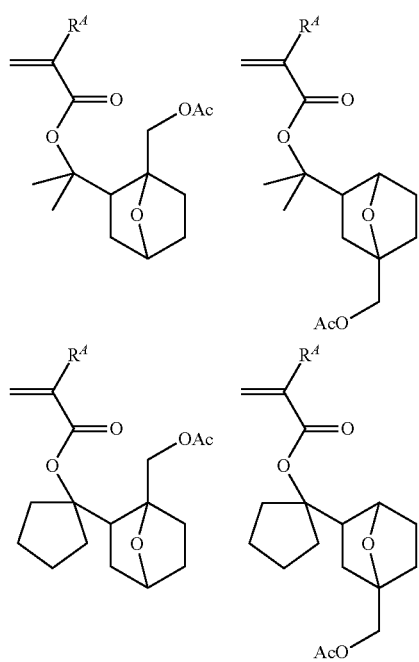

In a preferred embodiment, the polymer may further comprise recurring units (c) having an adhesive group. The adhesive group is selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is —S— or —NH—.

Examples of the monomer from which the recurring units (c) are derived are shown below, but not limited thereto. Herein $R^A$ is as defined above.

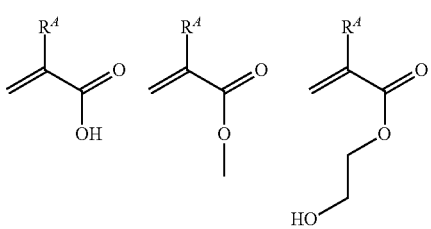

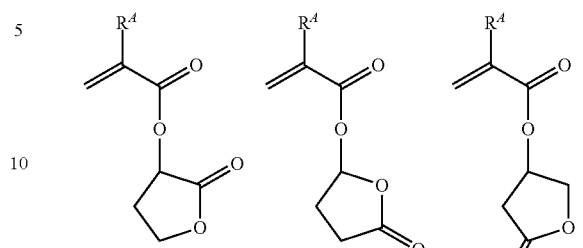

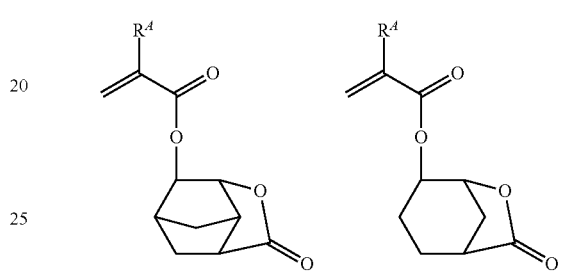

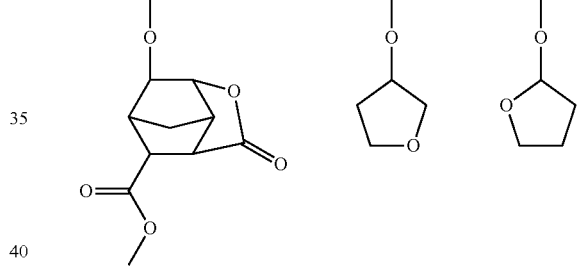

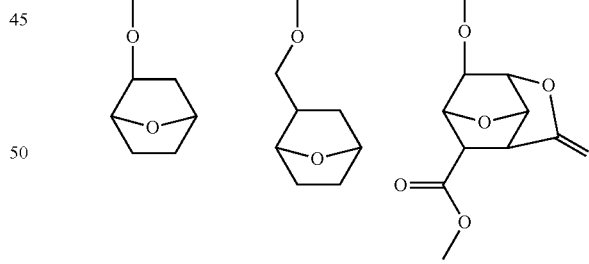

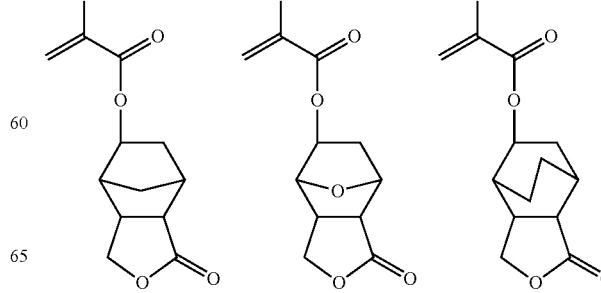

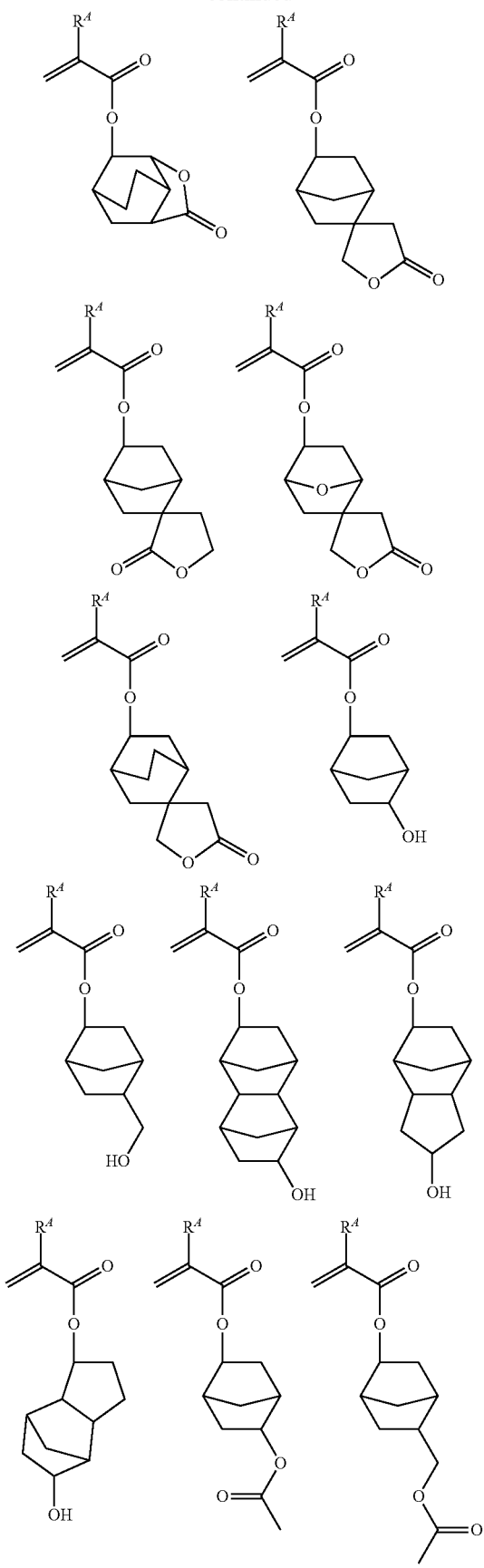
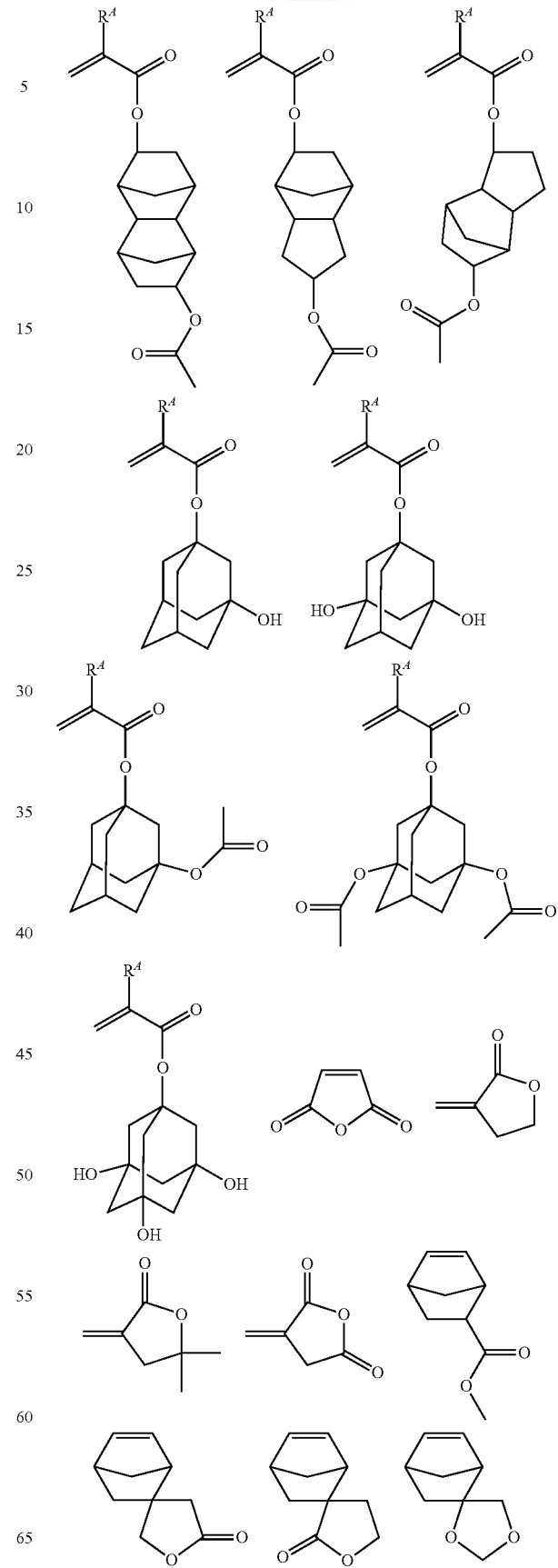

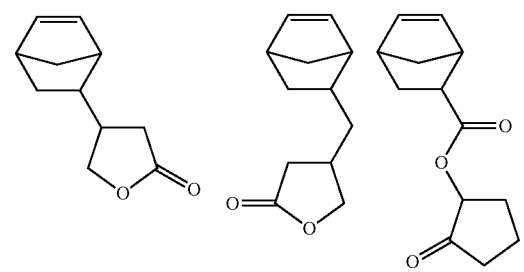
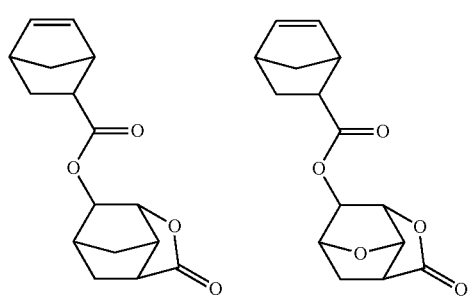
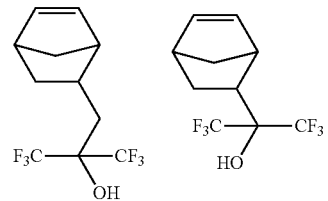
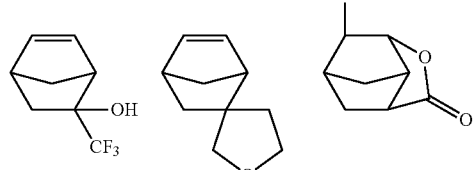
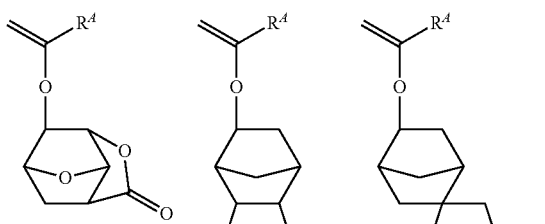
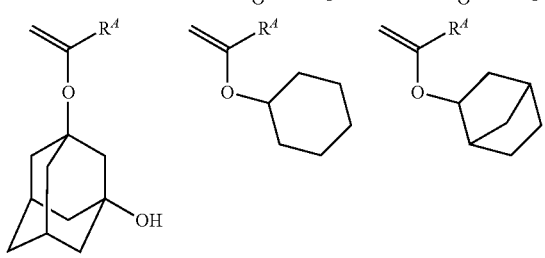
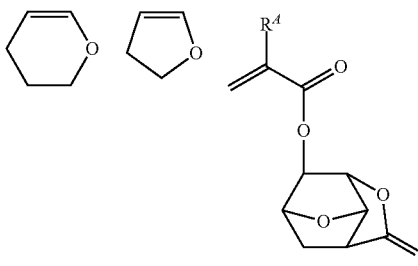
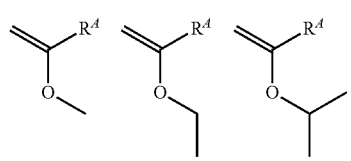
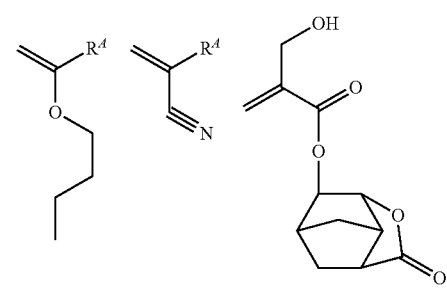
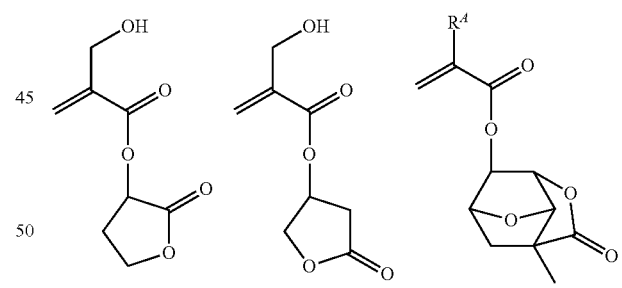
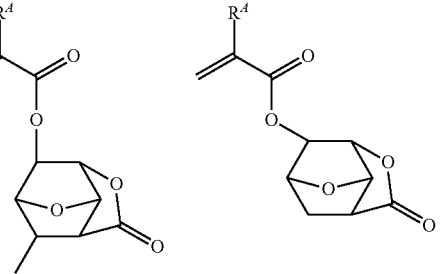

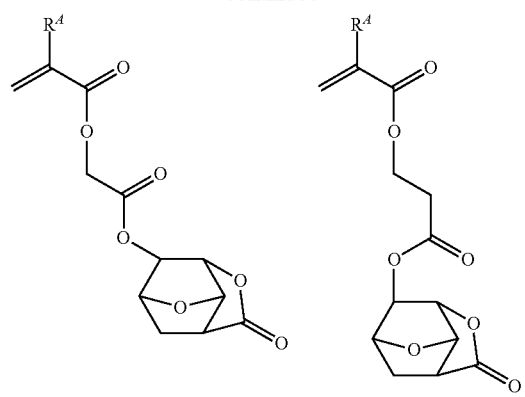
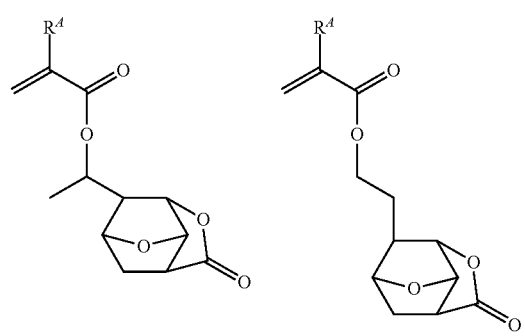
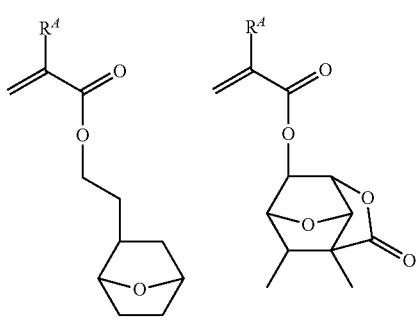
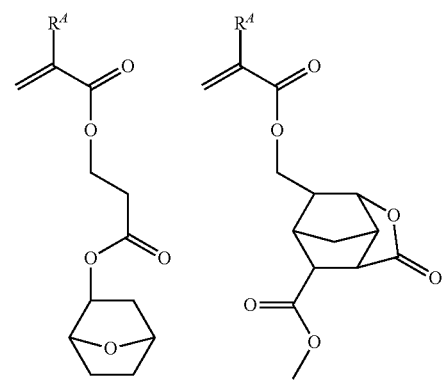
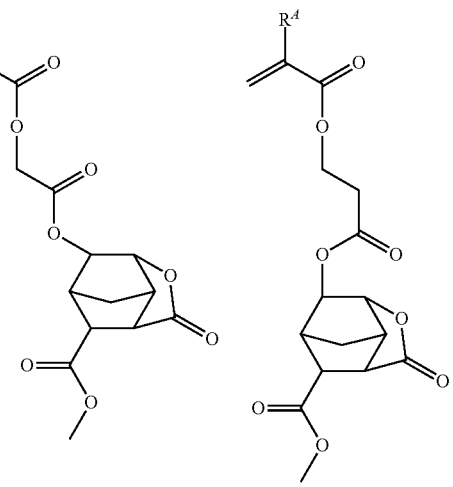

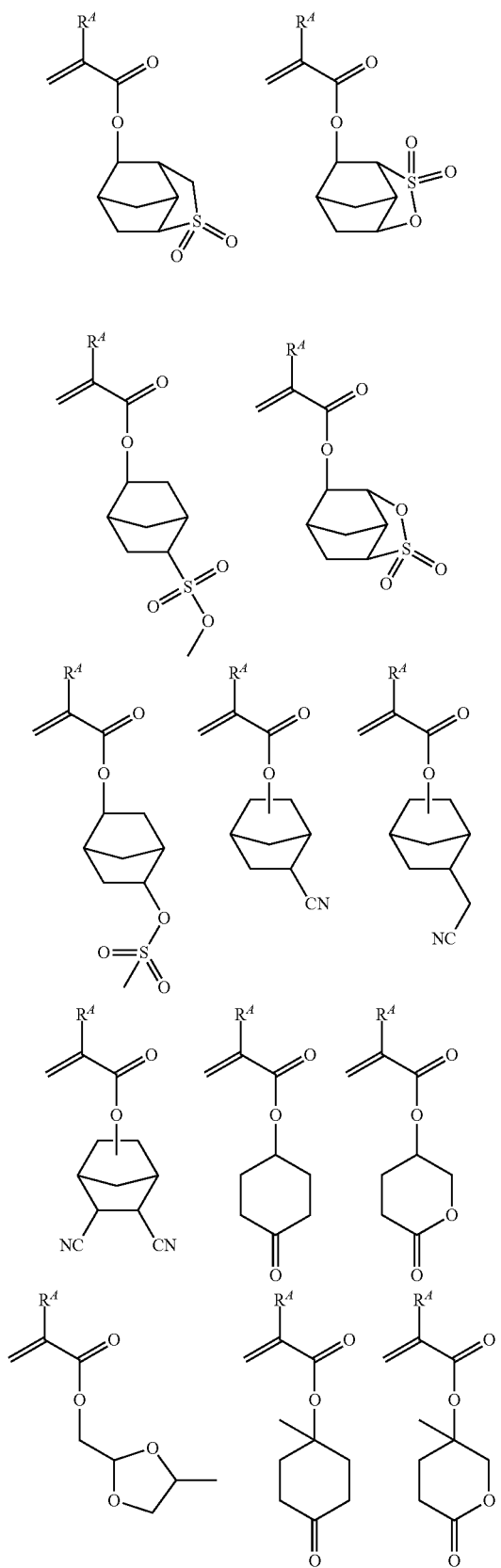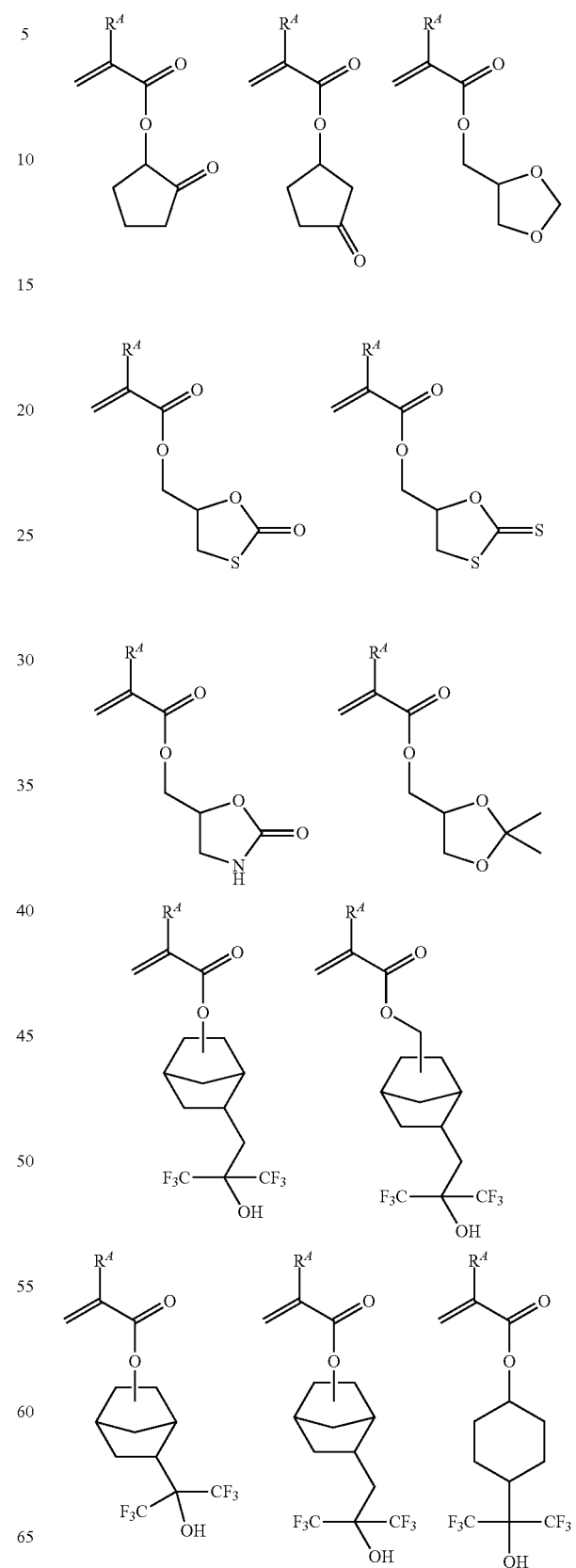

-continued
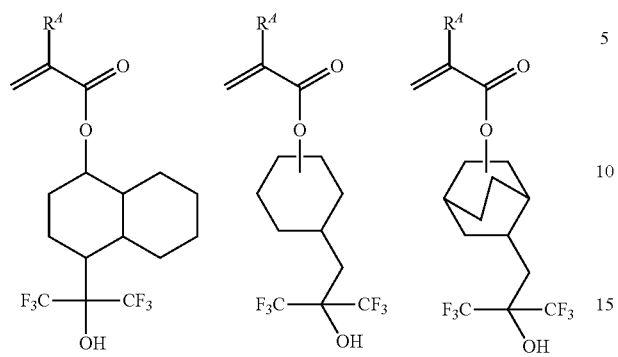
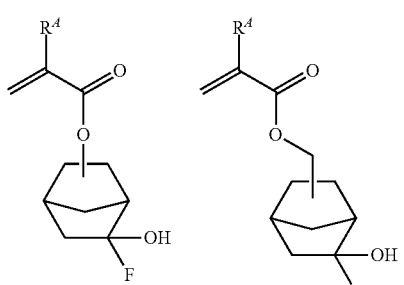
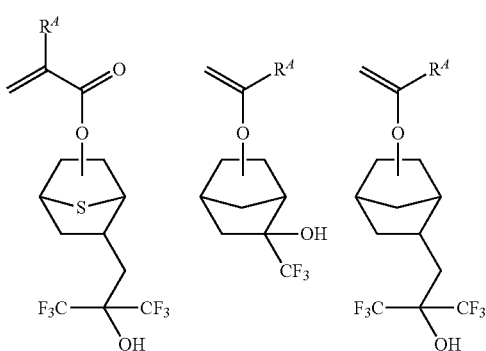
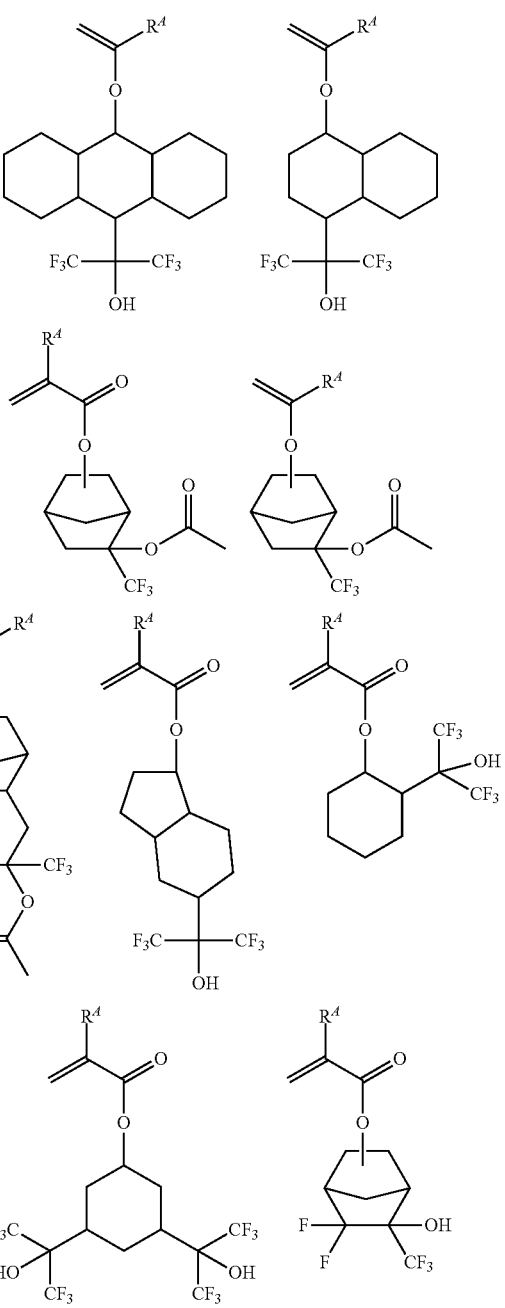
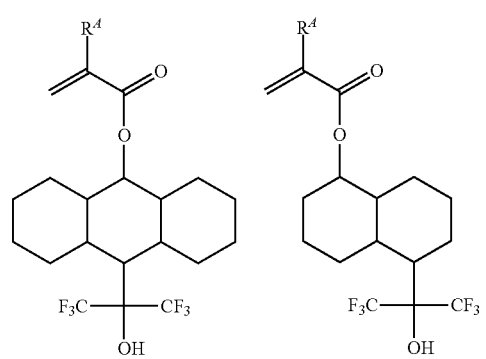
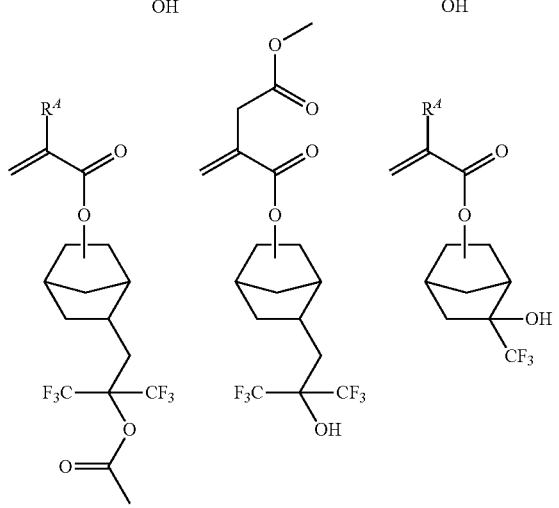

-continued
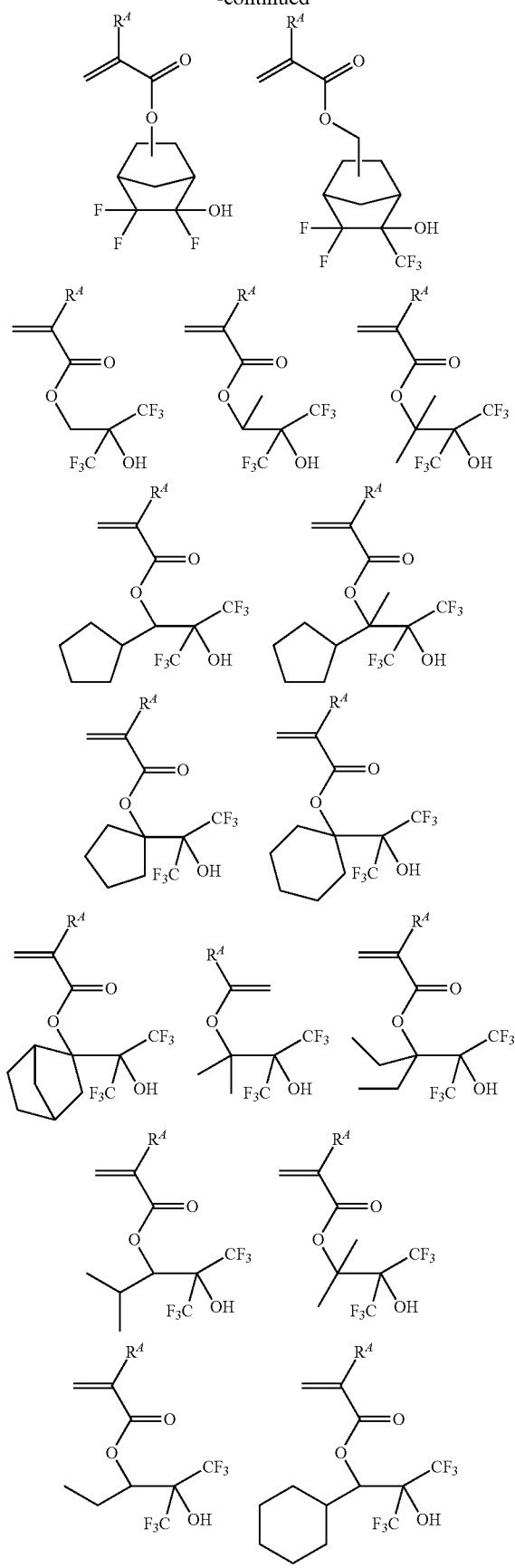
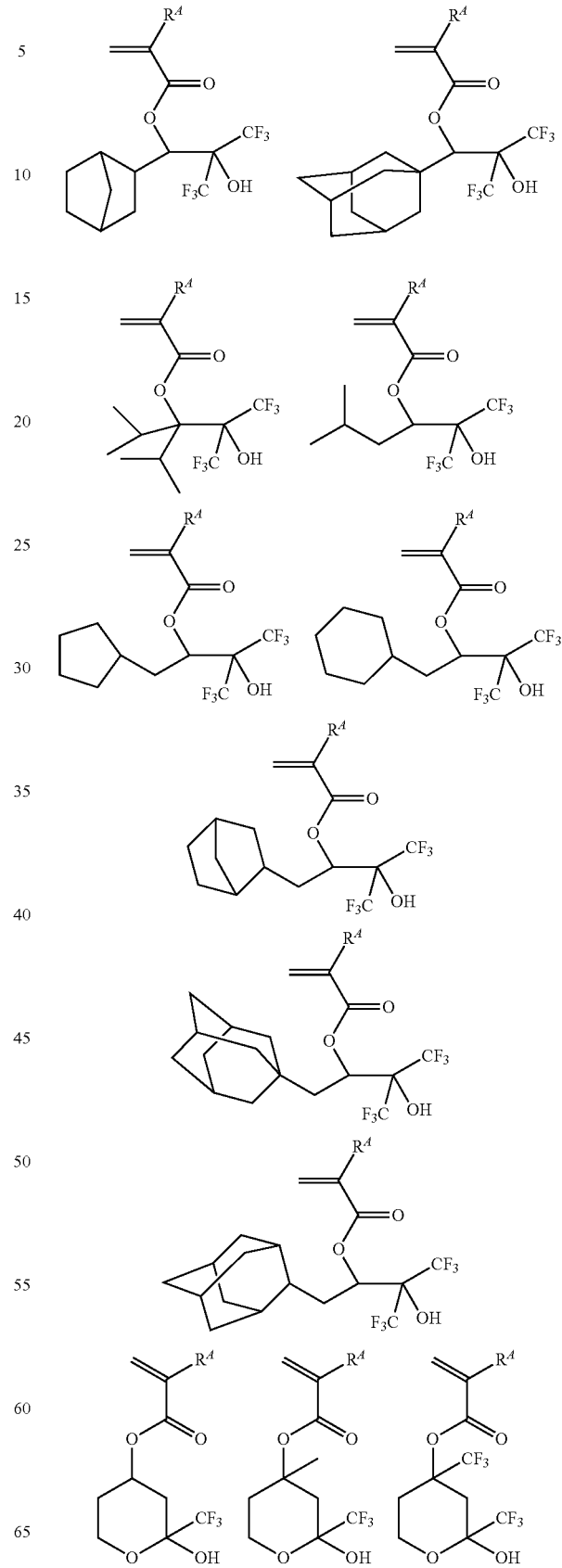

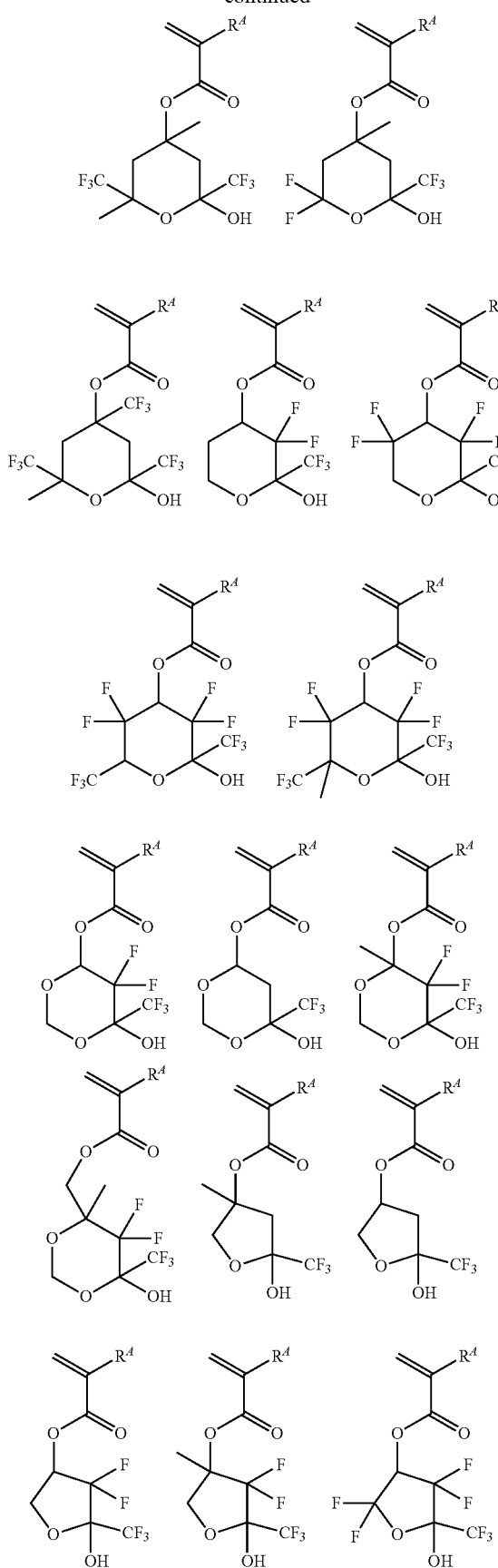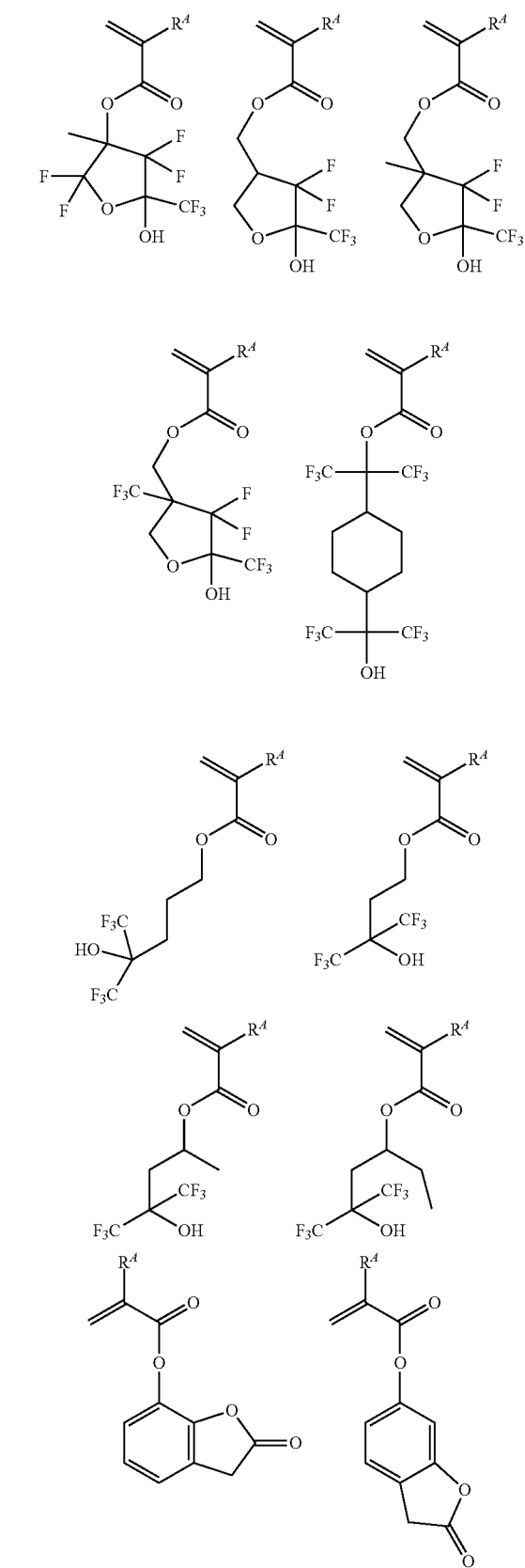

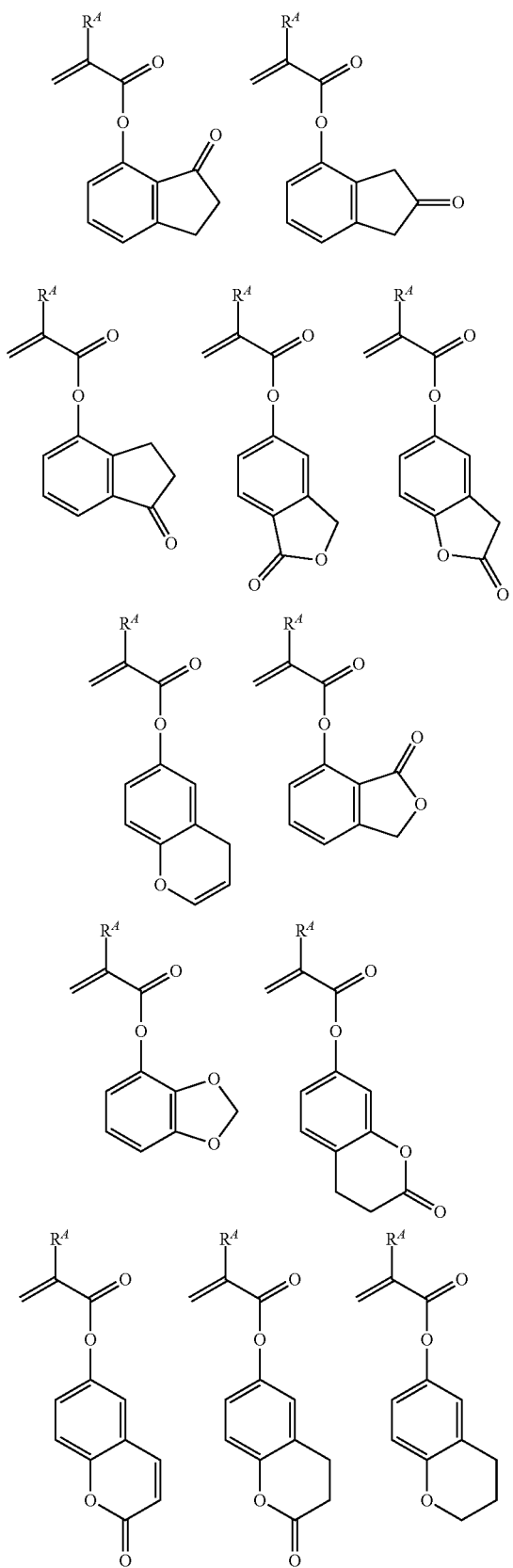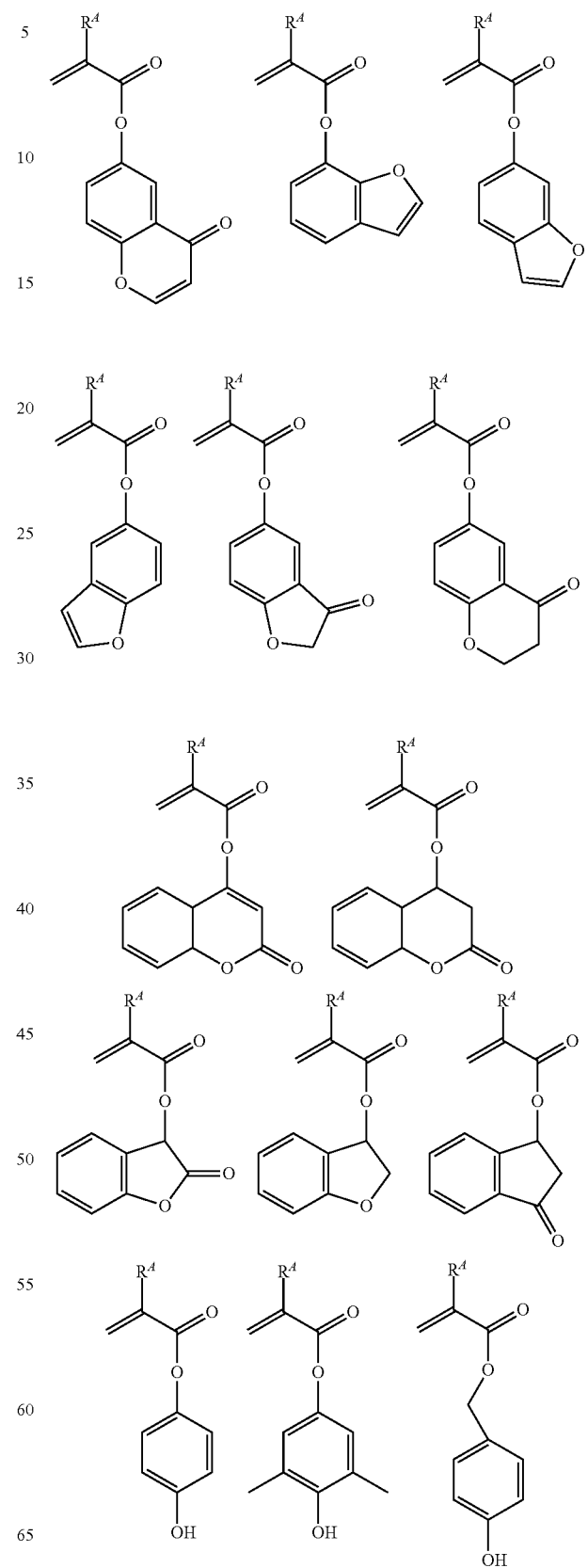

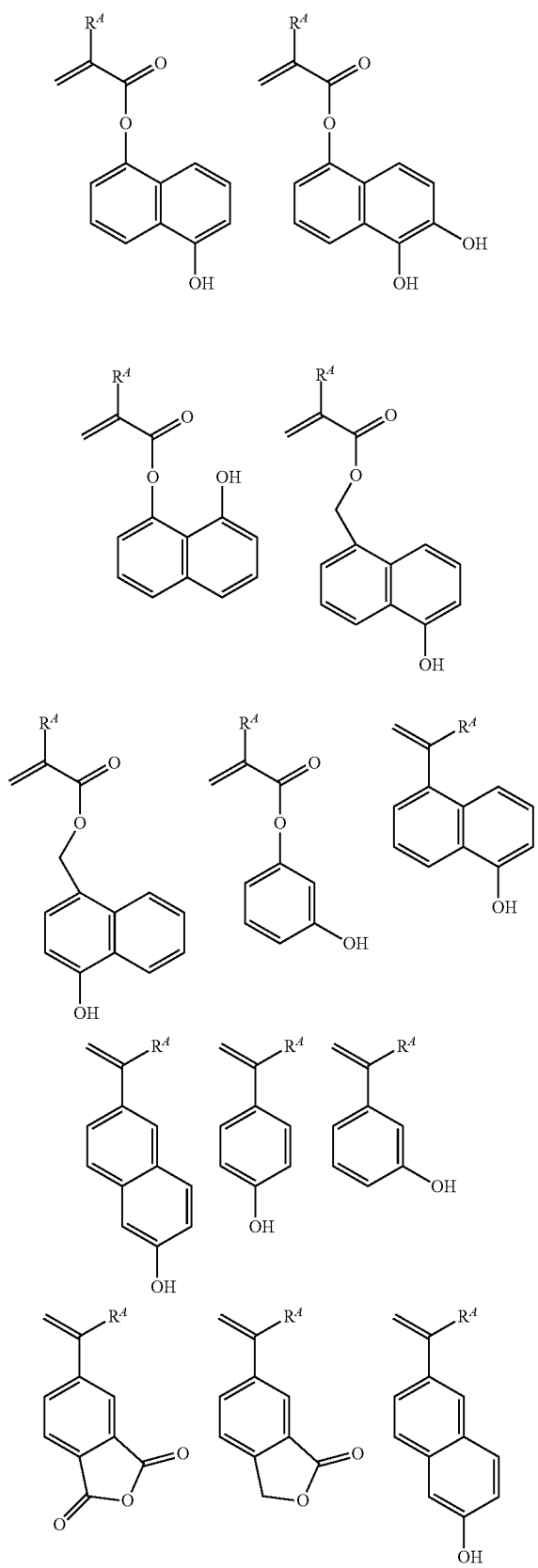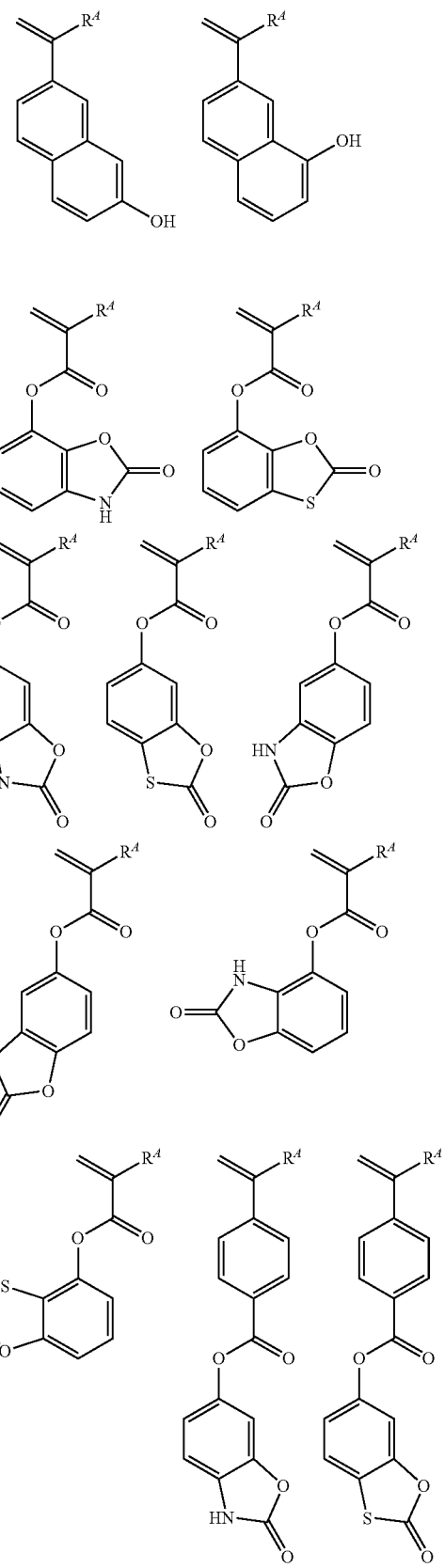

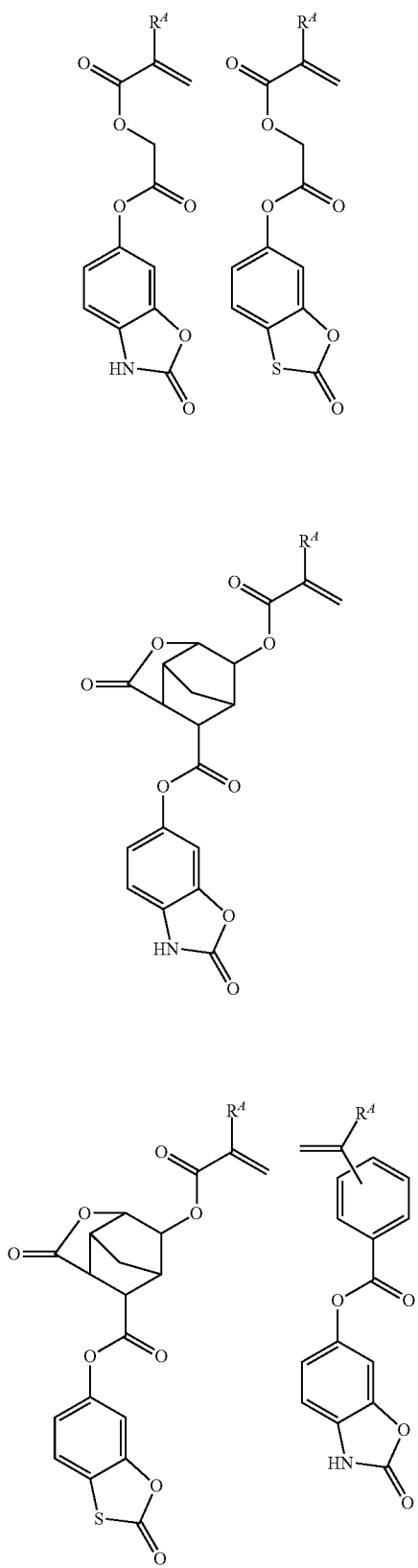

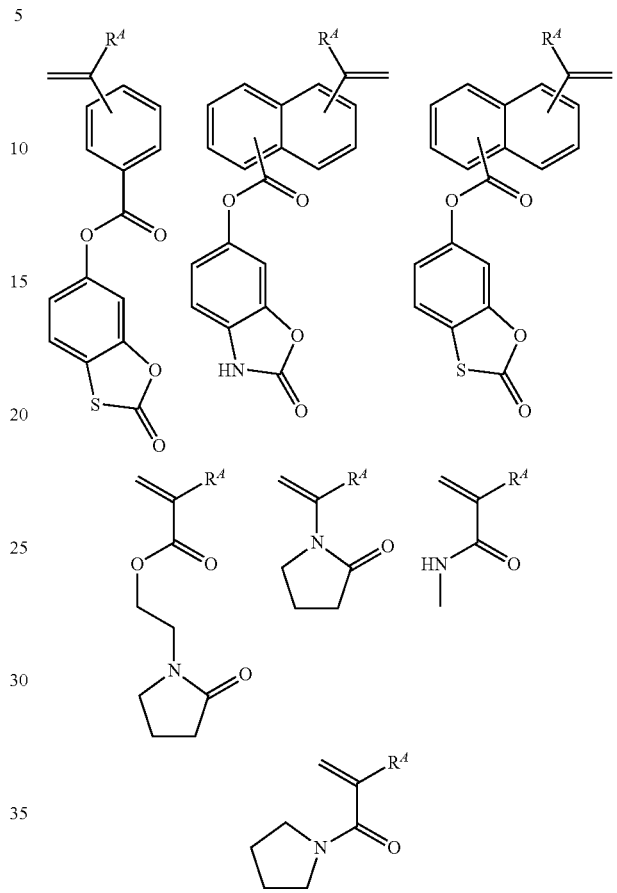

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

The polymer may further comprise recurring units of at least one type selected from recurring units having the formula (d1), recurring units having the formula (d2), and recurring units having the formula (d3). These recurring units are referred to as recurring to units (d1), (d2) and (d3), respectively.

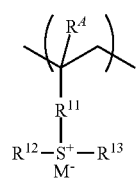

(d1)

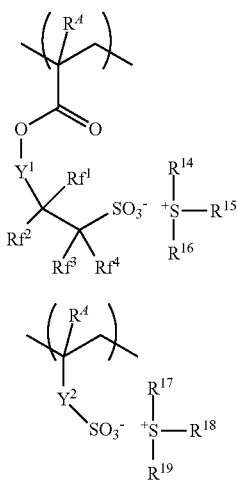

Herein $R^A$ is each independently hydrogen or methyl. $R^{11}$ is a single bond, phenylene group, —O—$R^{21}$—, or —C(=O)—$Z^1$—$R^{21}$—, wherein $Z^1$ is —O— or —NH—, $R^{21}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety. $Rf^1$ to $Rf^4$ are each independently fluorine, hydrogen or trifluoromethyl, at least one of $Rf^1$ to $Rf^4$ being fluorine. $R^{12}$ to $R^{19}$ are each independently a $C_1$-$C_2$ straight, branched or cyclic alkyl group which may contain a carbonyl, ester or ether moiety, $C_6$-$C_{12}$ aryl group, $C_7$-$C_{20}$ aralkyl group, or mecrcaptophenyl group. $Y^1$ is a single bond or a $C_1$-$C_{12}$ linking group which may contain an ester, other moiety or lactone ring. $Y^2$ is a single bond, methylene, ethylene, phenylene, fluorinated phenylene, —O—$R^{22}$—, or —C(=O)—$Z^2$—$R^{22}$—, wherein $Z^2$ is —O— or —NH—, $R^{22}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety. $M^-$ is a non-nucleophilic counter ion.

Examples of the non-nucleophilic counter ion represented by $M^-$ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Other non-nucleophilic counter ions include sulfonates having fluorine substituted at α-position as represented by the formula (K-1) and sulfonates having fluorine substituted at α- and β-positions as represented by the formula (K-2).

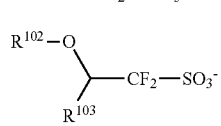

In formula (K-1), $R^{101}$ is hydrogen, or a $C_1$-$C_{20}$ straight, branched or cyclic alkyl group, $C_2$-$C_{20}$ straight, branched or cyclic alkenyl group, or $C_6$-$C_{20}$ aryl group, which may contain an ether, ester, carbonyl moiety, lactone ring or fluorine.

In formula (K-2), $R^{102}$ is hydrogen, or a $C_1$-$C_{30}$ straight, branched or cyclic alkyl group, $C_2$-$C_{30}$ straight, branched or cyclic acyl group, $C_2$-$C_{20}$ straight, branched or cyclic alkenyl group, $C_6$-$C_{20}$ aryl group or $C_6$-$C_{20}$ aryloxy group, which may have an ether, ester, carbonyl moiety or lactone ring. $R^{103}$ is hydrogen, methyl, ethyl or trifluoromethyl.

The recurring units (d1), (d2) and (d3) function as an acid generator. Binding an acid generator to the polymer backbone is effective for reducing acid diffusion and preventing the resolution from lowering due to blur by acid diffusion. Additionally, edge roughness is improved because the acid generator is uniformly dispersed.

The polymer may have further copolymerized therein recurring units (e) of any type selected from indene units (e1), acenaphthylene units (e2), chromone units (e3), coumarin units (e4) and norbornadiene units (e5) as shown below.

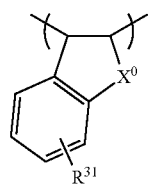

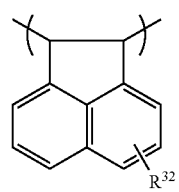

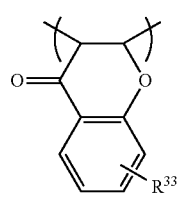

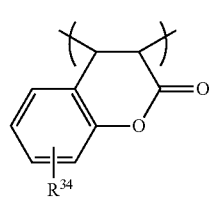

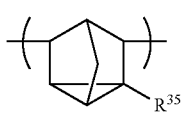

Herein $R^{31}$ to $R^{35}$ are each independently hydrogen, a $C_1$-$C_{30}$ straight, branched or cyclic alkyl group, $C_1$-$C_{30}$ straight, branched or cyclic halogenated alkyl group, hydroxyl group, $C_1$-$C_{30}$ straight, branched or cyclic alkoxy group, $C_2$-$C_{30}$ straight, branched or cyclic acyl group, $C_2$-$C_{30}$ straight, branched or cyclic alkoxycarbonyl group, $C_6$-$C_{10}$ aryl group, halogen, or 1,1,1,3,3,3-hexafluoro-2-propenol group. $X^0$ is methylene, oxygen or sulfur atom.

The polymer may further comprise recurring units (f) derived from styrene, vinylnaphthalene, vinylanthracene, vinylpyrene or methyleneindane.

In the polymer, recurring units (a) to (f) may be preferably incorporated in the following molar fraction:
$0<a<1.0$, $0\le b1<1.0$, $0\le b2<1.0$, $0<b1+b2<1.0$, $0\le c\le 0.9$, $0\le d1\le 0.5$, $0\le d2\le 0.5$, $0\le d3\le 0.5$, $0\le d1+d2+d3\le 0.5$, $0\le e1\le 0.5$, $0\le e2\le 0.5$, $0\le e3\le 0.5$, $0\le e4\le 0.5$, $0\le e5\le 0.5$, $0\le e1+e2+e3+e4+e5\le 0.5$, and $0\le f\le 0.5$;
more preferably $0.02\le a\le 0.8$, $0\le b1\le 0.7$, $0\le b2\le 0.7$, $0.1\le b1+b2\le 0.7$, $0<c\le 0.8$, $0\le d1\le 0.4$, $0\le d2\le 0.4$, $0\le d3\le 0.4$, $0\le d1+d2+d3\le 0.4$, $0\le e1\le 0.4$, $0\le e2\le 0.4$, $0\le e3\le 0.4$, $0\le e4\le 0.4$, $0\le e5\le 0.4$, $0\le e1+e2+e3+e4+e5\le 0.4$, and $0\le f\le 0.4$;
most preferably $0.05\le a\le 0.7$, $0\le b1\le 0.6$, $0\le b2\le 0.6$, $0.1\le b1+b2\le 0.6$, $0<c\le 0.7$, $0\le d1\le 0.3$, $0\le d2\le 0.3$, $0\le d3\le 0.3$, $0\le d1+d2+d3\times 0.3$, $0\le e1\le 0.3$, $0\le e2\le 0.3$, $0\le e3\le 0.3$, $0\le e4\le 0.3$, $0\le e5\le 0.3$, $0\le e1+e2+e3+e4+e5\le 0.3$, and $0\le f\le 0.3$; and
preferably, $a+b1+b2+c+d1+d2+d3+e1+e2+c3+c4+c5+f=1$.

The polymer serving as the base resin in the positive resist composition should have a weight average molecular weight (Mw) in the range of 1,000 to 500,000, and preferably 2,000 to 30,000, as measured versus polystyrene standards by gel permeation chromatography (GPC) using tetrahydrofuran (THF) as a solvent. With too low a Mw, the resist composition becomes less heat resistant. A polymer with too high a Mw loses alkaline solubility and gives rise to a footing phenomenon after pattern formation.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0, especially 1.0 to 1.5, in order to provide a resist composition suitable for micropatterning to a small feature size.

The polymer defined herein may be synthesized by any desired methods, for example, by dissolving suitable monomers selected from the monomers to form the recurring units (a) to (f) in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone, and γ-butyrolactone. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place, and the reaction time is 2 to 100 hours, more preferably 5 to 20 hours.

When hydroxystyrene or hydroxyvinylnaphthalene is copolymerized, an alternative method is possible. Specifically, acetoxystyrene or acctoxyvinylnaphthalene is used instead of hydroxystyrene or hydroxyvinylnaphthalene, and after polymerization, the acetoxy group is deprotected by alkaline hydrolysis as mentioned above, for thereby converting the polymer product to polyhydroxystyrene or hydroxypolyvinylnaphthalene. For alkaline hydrolysis, a base such as aqueous ammonia or triothylamine may be used. Preferably the reaction temperature is −20° C. to 100° C., more preferably 0° C. to 60° C., and the reaction time is 0.2 to 100 hours, more preferably 0.5 to 20 hours.

The positive resist composition is based on a base resin containing the polymer defined herein. A blend of two or more polymers which differ in compositional ratio, molecular weight or dispersity is also acceptable as the base resin.

While the polymer is used as a base resin, it is preferably combined with any desired components including an organic solvent, acid generator, dissolution regulator, basic compound, surfactant, and other additives to formulate a positive resist composition. This positive resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, yet better etching resistance, and minimal proximity bias because of restrained acid diffusion. By virtue of these advantages, the composition is fully useful in commercial application and suited as a pattern-forming material for the fabrication of VLSIs or photomasks. Particularly when an acid generator is added to formulate a chemically amplified positive resist composition capable of utilizing acid catalyzed reaction, the composition has a higher sensitivity and is further improved in the properties described above.

Examples of the organic solvent are described in JP-A 2008-111103, paragraphs [0144] to [0145] (U.S. Pat. No. 7,537,880). Suitable solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and dicthylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. An appropriate amount of the organic solvent used is 50 to 10,000 parts, more preferably 100 to 5,000 parts by weight per 100 parts by weight of the base resin.

An acid generator may be added to the positive resist composition so that it may function as a chemically amplified positive resist composition. Typical of the acid generator used herein is a photoacid generator (PAG) capable of generating an acid in response to actinic light or radiation. The PAG is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators, which may be used alone or in admixture. Exemplary PAGs are described in U.S. Pat. No. 7,537,880 (JP-A 2008-111103, paragraphs [0122]-[0142]). An appropriate amount of the acid generator added is 0.01 to 100 parts, more preferably 0.1 to 80 parts by weight per 100 parts by weight of the base resin.

A dissolution regulator may be added to the resist composition. The addition of the dissolution regulator to the resist composition is effective for exaggerating a difference in dissolution rate between exposed and unexposed regions, thus contributing to a further improvement in resolution. Exemplary dissolution regulators are described in U.S. Pat. No. 7,771,914 (JP-A 2008-122932, paragraphs [0155]-[0178]). An appropriate amount of the dissolution regulator added is 0 to 50 parts, more preferably 0 to 40 parts by weight per 100 parts by weight of the base resin.

A basic compound may be added to the resist composition. The addition of the basic compound to the resist composition is effective, for example, for reducing the rate of acid diffusion in the resist film, thus contributing to a further improvement in resolution. Exemplary basic compounds include primary, secondary and tertiary amine compounds, specifically amine compounds having a hydroxyl, ether, ester, lactone, cyano or sulfonic ester group, as described in JP-A 2008-111103, paragraphs [0146]-[0164] (U.S. Pat. No. 7,537,880) and compounds having a carbamate group as described in JP 3790649. Also useful are quenchers of polymer type as described in JP-A 2008-239918 (U.S. Pat. No. 7,598,016). The polymeric quencher segregates at the resist surface after coating and thus enhances the rectangularity of resist pattern. In the immersion lithography where a protective film is applied on the resist film, the polymeric quencher is also effective for preventing any film thickness loss of resist pattern or rounding of pattern top. An appropriate amount of the basic compound added is 0 to 100 parts, more preferably 0.001 to 50 parts by weight per 100 parts by weight of the base resin.

A surfactant may be added to the resist composition. The addition of the surfactant to the resist composition is effective for facilitating or controlling coating operation. Exemplary surfactants are described in JP-A 2008-111103, paragraphs [0165]-[0166]. An appropriate amount of the surfactant added is 0 to 10 parts, more preferably 0.0001 to 5 parts by weight per 100 parts by weight of the base resin.

An acetylene alcohol may be added to the resist composition. Exemplary acetylene alcohols are described in JP-A 2008-122932, paragraphs [0179]-[0182]. An appropriate amount of the acetylene alcohol added is 0 to 5 parts by weight per 100 parts by weight of the base resin.

Process

The positive resist composition may be used in the fabrication of various integrated circuits. Pattern formation using the resist composition may be performed by well-known lithography processes. The process generally involves coating, prebake, exposure, and development. If necessary, any additional steps may be added.

Specifically, the positive resist composition is first applied onto a substrate on which an integrated circuit is to be formed (e.g., Si, $SiO_2$, SiN, SiON, TIN, WSi, BPSG, SOG, or organic antireflective coating) or a substrate on which a mask circuit is to be formed (e.g., Cr, CrO, CrON or $MoSi_2$) by a suitable coating technique such as spin coating, roll coating, flow coating, dip coating, spray coating or doctor coating. The coating is prebaked on a hot plate preferably at a temperature of 60 to 150° C. for 10 seconds to 30 minutes, more preferably at 80 to 120° C. for 30 seconds to 20 minutes. The resulting resist film is generally 0.01 to 2.0 µm thick.

If desired, a protective film may be formed on the resist film. The protective film is preferably formed of an alkaline developer-soluble composition so that both formation of a resist pattern and stripping of the protective film may be achieved during development. The protective film has the functions of restraining outgassing from the resist film, filtering or cutting off out-of-band (OOB) light having a wavelength of 140 to 300 nm emitted by the EUV laser (other than 13.5 nm), and preventing the resist film from assuming T-top profile or from losing its thickness under environmental impacts.

The resist film is then exposed to a desired pattern of high-energy radiation such as UV, deep-UV, EUV (wavelength 3 to 15 nm), EB, x-ray, soft x-ray, excimer laser light, γ-ray or synchrotron radiation directly or through a mask. The exposure dose is preferably about 1 to 200 $mJ/cm^2$, more preferably about 10 to 100 $mJ/cm^2$, or 0.1 to 100 $\mu C/cm^2$, more preferably 0.5 to 50 $\mu C/cm^2$. The resist film may be further baked (PEB) on a hot plate preferably at 60 to 150° C. for 10 seconds to 30 minutes, more preferably at 80 to 120° C. for 30 seconds to 20 minutes. Notably PEB is optional.

Thereafter the resist film is developed in a developer for 3 seconds to 3 minutes, preferably 5 seconds to 2 minutes by conventional techniques such as dip, puddle and spray techniques. The resist film in the exposed area is dissolved in the developer whereas the resist film in the unexposed area is not dissolved. In this way, the desired positive pattern is formed on the substrate. It is appreciated that the resist composition of the invention is best suited for micropatterning using such high-energy radiation as EB, EUV, x-ray, soft x-ray, γ-ray and synchrotron radiation among others.

Suitable developers are 0.1 to 10 wt %, preferably 2 to 5 wt % aqueous solutions of tetramethylammonium hydroxide (TMAH), tetraethylammonium hydroxide (TEAH), tetrapropylammonium hydroxide (TPAH) and tetrabutylammonium hydroxide (TBAH). Using the developer in the form of an alkaline aqueous solution, a positive resist pattern is formed.

Although TMAH aqueous solution is generally used as the developer, TEAH, TPAH and TBAH having a longer alkyl chain are effective in inhibiting the resist film from being swollen during development and thus preventing pattern collapse. The TMAH developer is most often used as 2.38 wt % aqueous solution, which corresponds to 0.26N. The TEAH, TPAH, and TBAH aqueous solutions should preferably have an equivalent normality. The concentration of TEAH, TPAH, and TBAH that corresponds to 0.26N is 3.84 wt %, 5.31 wt %, and 6.78 wt %, respectively.

When a pattern with a line size of 32 nm or less is resolved by the EB and EUV lithography, there arises a phenomenon that lines become wavy, lines merge together, and merged lines collapse. It is believed that this phenomenon occurs because lines are swollen in the developer and the thus expanded lines merge together. Since the swollen lines containing liquid developer are as soft as sponge, they readily collapse under the stress of rinsing. For this reason, the developer using a long-chain alkyl developing agent is effective for preventing film swell and hence, pattern collapse.

In another embodiment, an organic solvent is used as the developer. A negative pattern can be formed from the resist composition by organic solvent development. The developer used to this end is at least one solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxylsobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, tert-butylbenzene, and mesitylene. The solvents may be used alone or in admixture.

EXAMPLE

Synthesis Examples, Comparative Synthesis Examples, Examples and Comparative Examples are given below for further illustrating the invention, but they should not be construed as limiting the invention thereto. Mw is a weight average molecular weight as measured versus polystyrene standards by GPC using tetrahydrofuran (THF) solvent, and Mw/Mn designates molecular weight distribution or dispersity. The composition of a polymer is analyzed by $^{13}$C- and $^1$H-NMR spectroscopy. All parts (pbw) are by weight.

1) Synthesis of Monomer

Synthesis Example 1

Synthesis of Monomer 1

Monomer 1

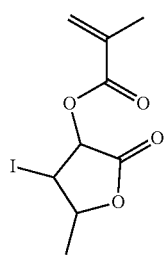

To 500 g of THF were added 110 g of 3-hydroxy-4-iodo-5-methyloxolan-2-one and 3.7 g of 4-(dimethylamino)pyridine. Under ice cooling, 92.4 g of methacrylic anhydride was added dropwise to the solution. The solution was stirred at room temperature for 5 hours. Then water was added to quench the reaction, followed by standard aqueous workup. The product was purified by silica gel column chromatography, obtaining 91 g (yield 65%) of Monomer 1.

2) Synthesis of Polymers

PAG Monomers 1 to 3 used in the following Synthesis Examples are identified below.

PAG Monomer 1

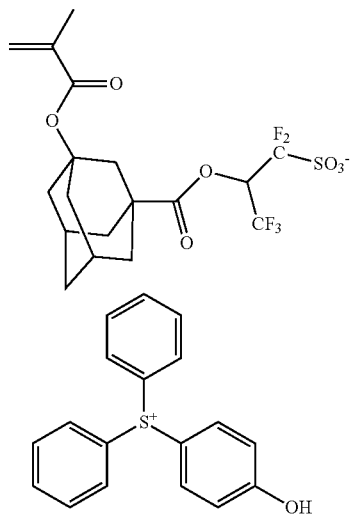

PAG Monomer 2

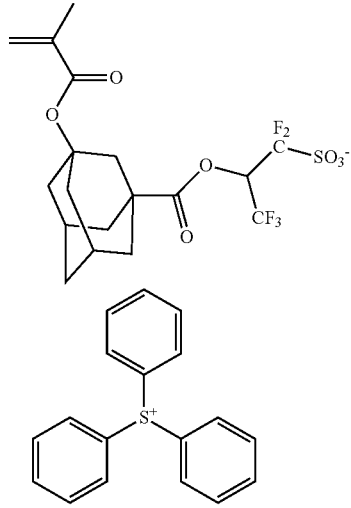

PAG Monomer 3

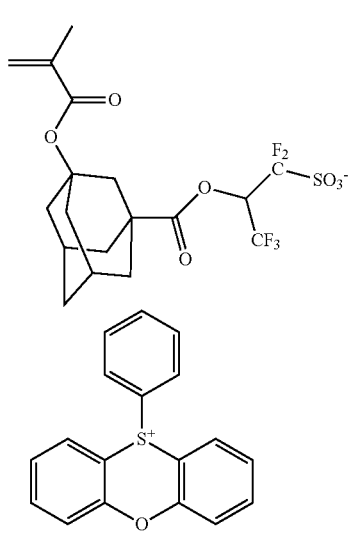

Synthesis Example 2

Synthesis of Polymer 1

A 2-L flask was charged with 8.2 g of ethylcyclopentyl methacrylate, 3.6 g of 4-hydroxyphenyl methacrylate, 155 g of Monomer 1, and 40 g of THF. The reactor was cooled at −70° C. in nitrogen atmosphere, after which vacuum pumping and nitrogen blow were repeated three times. The reactor was warmed up to room temperature, whereupon 1.2 g of azobisisobutyronitrile (AIBN) as polymerization initiator was added. The reactor was heated at 60° C., whereupon reaction ran for 15 hours. The reaction solution was poured into 1 L of isopropyl alcohol (IPA) whereupon white solids precipitated. The precipitate was filtered and dried in vacuum at 60° C., yielding Polymer 1.

Polymer 1

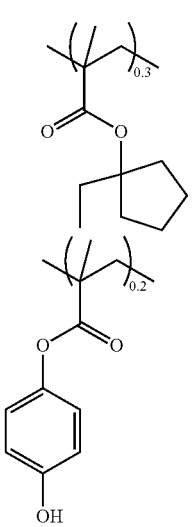

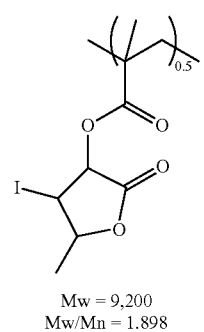

Mw = 9,200
Mw/Mn = 1.898

Synthesis Example 3

Synthesis of Polymer 2

A 2-L flask was charged with 5.2 g of 1-(adamantan-1-yl)-1-methylethyl methacrylate, 2.9 g of t-pentyloxystyrene, 3.6 g of 4-hydroxyphenyl methacrylate, 6.2 g of Monomer 1, 11.0 g of PAG Monomer 2, and 40 g of THF. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of IPA whereupon white solids precipitated. The precipitate was filtered and dried in vacuum at 60° C., yielding Polymer 2.

Polymer 2

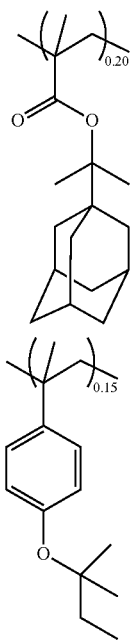

-continued

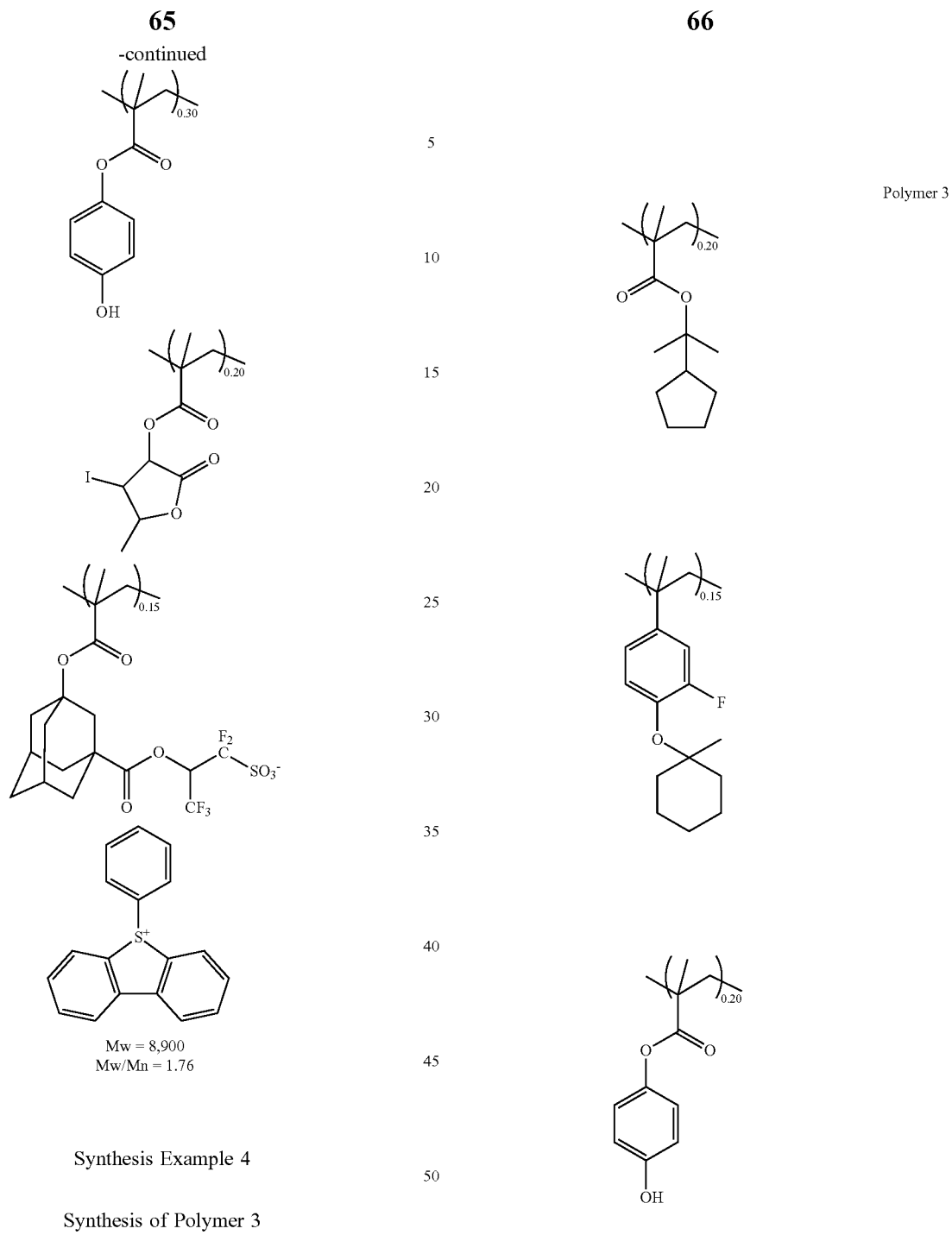

Mw = 8,900
Mw/Mn = 1.76

Synthesis Example 4

Synthesis of Polymer 3

A 2-L flask was charged with 5.2 g of 1-(cyclopropylen-1-yl)-1-methylethyl methacrylate, 3.5 g of 3-fluoro-4-(methylcyclohexyloxy)styrene, 5.3 g of 4-hydroxyphenyl methacrylate, 7.8 g of Monomer 1, 15.0 g of PAG Monomer 3, and 40 g of THF. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of IPA whereupon white solids precipitated. The precipitate was filtered and dried in vacuum at 60° C., yielding Polymer 3.

Polymer 3

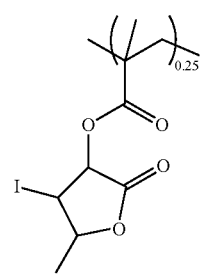

-continued

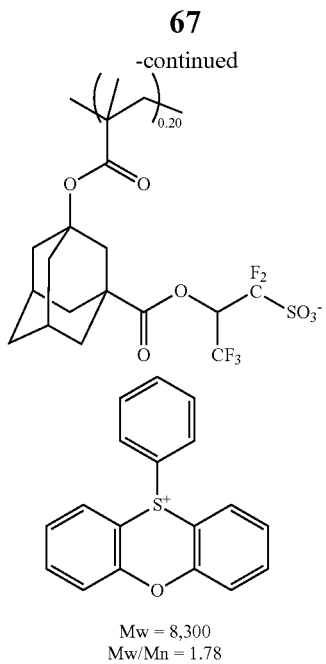

Mw = 8,300
Mw/Mn = 1.78

Synthesis Example 5

Synthesis of Polymer 4

A 2-L flask was charged with 8.2 g of 3-ethyl-3-exo-tetracyclo[4.4.0.1$^{2,5}$.1$^{7,10}$]dodecanyl methacrylate, 3.6 g of 4-hydroxyphenyl methacrylate, 10.9 g of Monomer 1, 11.5 g of PAG Monomer 1, and 40 g of THF. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of IPA whereupon white solids precipitated. The precipitate was filtered and dried in vacuum at 60° C., yielding Polymer 4.

Polymer 4

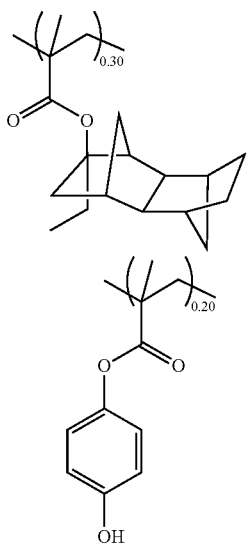

-continued

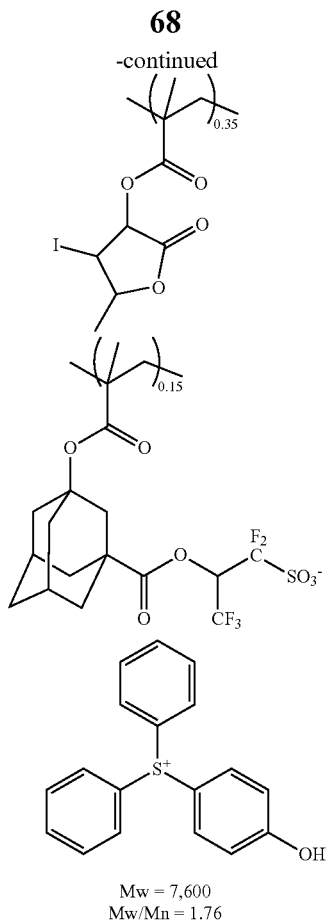

Mw = 7,600
Mw/Mn = 1.76

Synthesis Example 6

Synthesis of Polymer 5

A 2-L flask was charged with 8.4 g of 1-t-butyl-1-cyclopentyl methacrylate, 3.6 g of 4-hydroxyphenyl methacrylate, 6.2 g of Monomer 1, 1.0 g of α-methylene-γ-butyrolactone, 11.0 g of PAG Monomer 2, and 40 g of THF. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of IPA whereupon white solids precipitated. The precipitate was filtered and dried in vacuum at 60° C., yielding Polymer 5.

Polymer 5

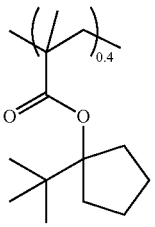

-continued

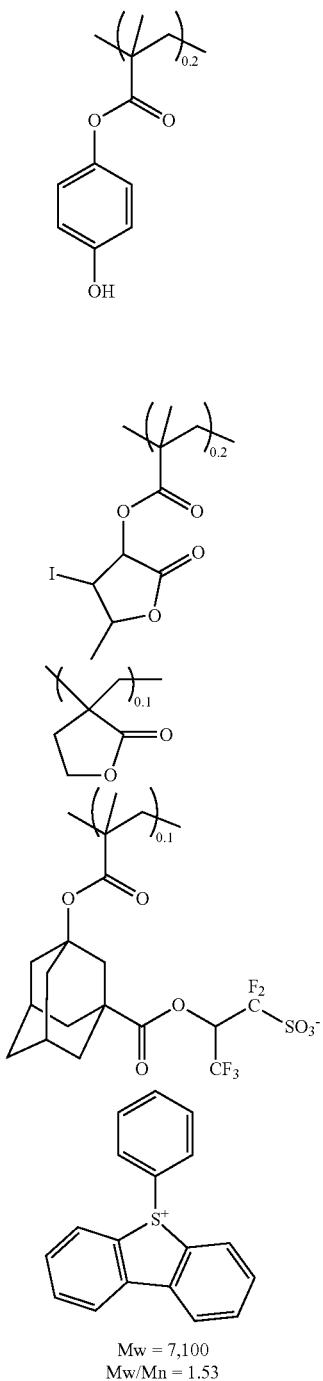

Comparative Synthesis Example 1

Synthesis of Comparative Polymer 1

Comparative Polymer 1 was synthesized by the same procedure as in Synthesis Example 2 aside from using 6.8 g of 2-oxotetrahydrofuran-3-yl methacrylate instead of Monomer 1.

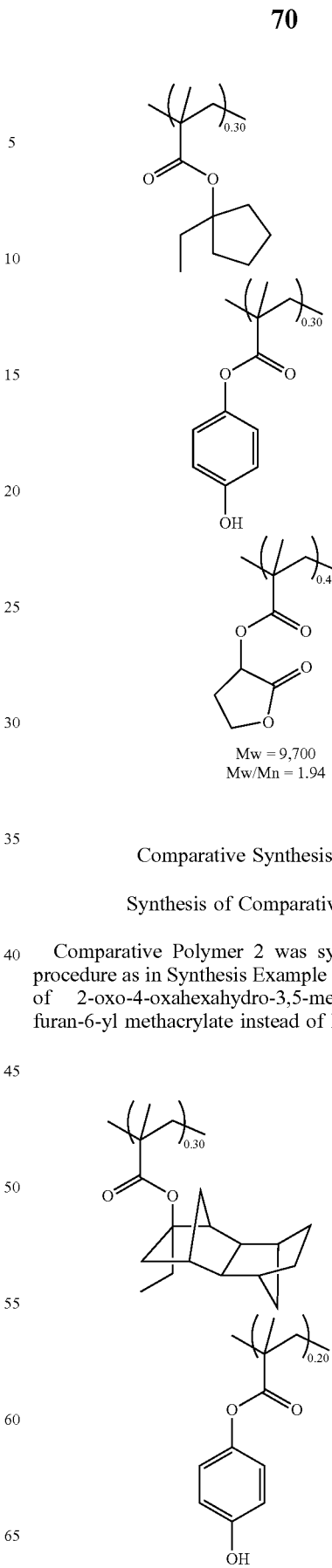

Mw = 9,700
Mw/Mn = 1.94

Comparative Synthesis Example 2

Synthesis of Comparative Polymer 2

Comparative Polymer 2 was synthesized by the same procedure as in Synthesis Example 5 aside from using 7.8 g of 2-oxo-4-oxahexahydro-3,5-methano-2H-cyclopenta[b]furan-6-yl methacrylate instead of Monomer 1.

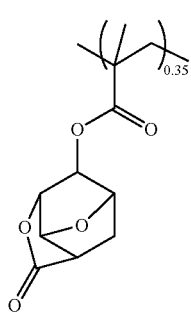

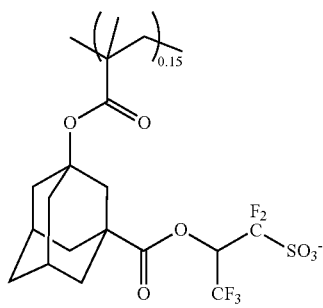

Mw = 7,300
Mw/Mn = 1.88

Examples 1 to 8 and Comparative Examples 1 and 2

3) Preparation of Resist Compositions

Positive resist compositions were prepared by dissolving selected components in a solvent in accordance with the recipe shown in Table 1, and filtering through a filter having a pore size of 0.2 μm. The solvent contained 100 ppm of a surfactant FC-4430 (3M).

The components in Table 1 are as identified below.

Polymers 1 to 5: polymers synthesized in Synthesis Examples 2 to 6

Comparative Polymers 1 and 2: polymers synthesized in Comparative Synthesis Examples 1 and 2

Organic solvents: propylene glycol monomethyl ether acetate (PGMEA) propylene glycol monomethyl ether (PGME) cyclohexanone (CyH) diacetone alcohol (DAA)

Acid generators: PAG1 to PAG4 of the following structural formulae

Basic compound: Quencher 1 of the following structural formula

PAG 1

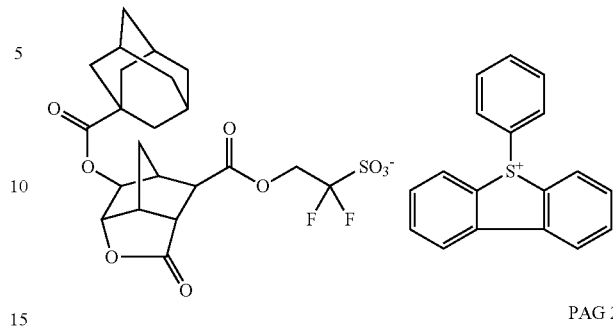

PAG 2

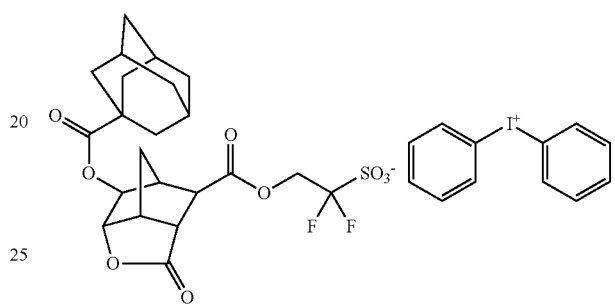

PAG 3

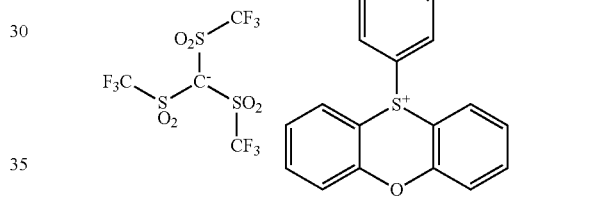

PAG 4

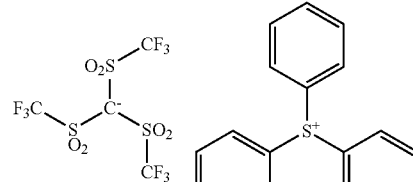

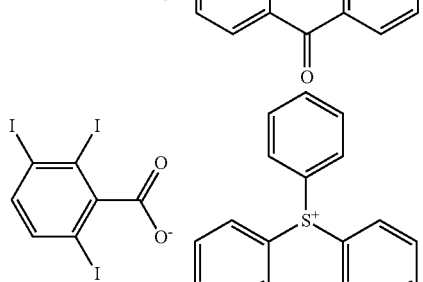

Quencher 1

4) EUV Exposure Test

The positive resist composition was spin coated on a silicon substrate having a silicon-containing spin-on hard mask SHB-A940 (Si content 43 wt %) coating of 20 nm thick and prebaked on a hot plate at 105° C. for 60 seconds to form a resist film of 60 am thick. Using an EUV scanner NXE3300 (ASML, NA 0.33, σ0.9/0.6, quadrupole illumination), the resist film was exposed to EUV through a mask bearing a hole pattern at a pitch 46 nm (on-wafer size) and +20% bias. The resist film was baked (PEB) on a hot plate at the temperature shown in Table 1 for 60 seconds and developed in a 2.38 wt % TMAH aqueous solution for 30 seconds to form a hole pattern having a size of 23 nm.

The resist pattern was evaluated. The size of 50 holes was measured under CD-SEM (CG-5000, Hitachi, Ltd.), from which a size variation (3σ) was computed and reported as CDU. The exposure dose that provides a hole pattern having a size of 23 nm is reported as sensitivity.

The resist composition is shown in Table 1 together with the sensitivity and CDU of EUV lithography.

TABLE 1

| | Polymer (pbw) | Acid generator (pbw) | Basic compound (pbw) | Organic solvent (pbw) | PEB temp. (° C.) | Sensitivity (mJ/cm$^2$) | CDU (nm) |
|---|---|---|---|---|---|---|---|
| Example 1 | Polymer 1 (100) | PAG 1 (25.0) | Quencher 1 (3.00) | PGMEA(400) CyH(2,000) PGME(100) | 80 | 20 | 4.0 |
| Example 2 | Polymer 2 (100) | — | Quencher 1 (3.00) | PGMEA(400) CyH(2,000) PGME(100) | 80 | 22 | 3.7 |
| Example 3 | Polymer 3 (100) | — | Quencher 1 (3.00) | PGMEA(2,000) DAA(500) | 80 | 20 | 3.1 |
| Example 4 | Polymer 4 (100) | — | Quencher 1 (3.00) | PGMEA(2,000) DAA(500) | 85 | 18 | 2.8 |
| Example 5 | Polymer 5 (100) | PAG 1 (6.0) | Quencher 1 (3.00) | PGMEA(2,000) DAA(500) | 80 | 19 | 2.7 |
| Example 6 | Polymer 5 (100) | PAG 2 (6.0) | Quencher 1 (3.00) | PGMEA(2,000) DAA(500) | 80 | 17 | 2.4 |
| Example 7 | Polymer 5 (100) | PAG 3 (5.0) | Quencher 1 (3.80) | PGMEA(2,000) DAA(500) | 80 | 22 | 2.2 |
| Example 8 | Polymer 5 (100) | PAG 4 (5.0) | Quencher 1 (3.80) | PGMEA(2,000) DAA(500) | 80 | 24 | 2.1 |
| Comparative Example 1 | Comparative Polymer 1 (100) | PAG 1 (25.0) | Quencher 1 (3.00) | PGMEA(400) CyH(2,000) PGME(100) | 80 | 33 | 5.2 |
| Comparative Example 2 | Comparative Polymer 2 (100) | — | Quencher 1 (3.00) | PGMEA(2,000) DAA(500) | 90 | 23 | 4.7 |

It is evident from Table 1 that the positive resist compositions within the scope of the invention exhibit satisfactory resolution and sensitivity and reduced CDU. When polymers containing recurring units (d1) to (d3) are used as the base resin, CDU is further reduced.

Japanese Patent Application No. 2016-128886 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A pattern forming process comprising the steps of coating a positive resist composition onto a substrate, baking to form a resist film, exposing the resist film to high-energy radiation, and developing the exposed resist film in a developer, wherein the high-energy radiation is EB or EUV, wherein the positive resist composition comprises a base resin containing a polymer comprising recurring units (a) having the formula (a), and recurring units (b1) having a carboxyl group whose hydrogen is substituted by an acid labile group and/or recurring units (b2) having a phenolic hydroxyl group whose hydrogen is substituted by an acid labile group, an organic solvent and an acid generator, and an organic solvent, the polymer having a weight average molecular weight, of 1,000 to 500,000,

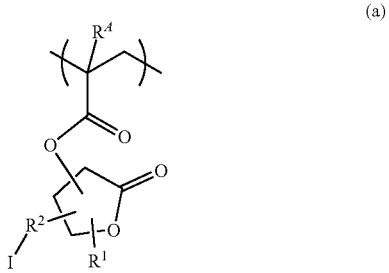

wherein $R^A$ is hydrogen or methyl, $R^1$ is hydrogen or $C_1$-$C_4$ straight or branched alkyl, and $R^2$ is a single bond or methylene.

2. A pattern forming process comprising the steps of coating a positive resist composition onto a substrate, baking to form a resist film, exposing the resist film to high-energy radiation, and developing the exposed resist film in a developer, wherein the high-energy radiation is EB or EUV, wherein the positive resist composition comprises a base resin containing a polymer comprising recurring units (a) having the formula (a), recurring units (b1) having a carboxyl group whose hydrogen is substituted by an acid labile group andior recurring, units (b2) having a phenolic hydroxyl group whose hydrogen is substituted by an acid labile group and recurring units of at least one type selected from recurring units having the formulae (d1), (d2) and (d3) as an acid generator, and an organic solvent, the polymer having a weight, average molecular weight of 1,000 to 500,000,

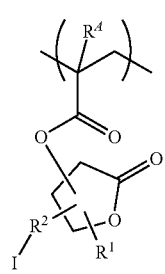

(a)

wherein $R^A$ is hydrogen or methyl, $R^1$ is hydrogen or $C_1$-$C_4$ straight or branched alkyl, and $R^2$ is a single bond or methylene,

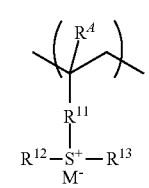

(d1)

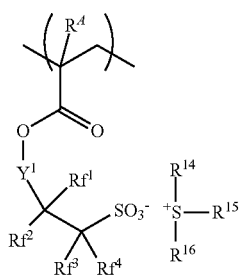

(d2)

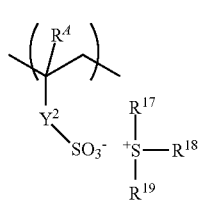

(d3)

wherein $R^A$ is each independently hydrogen or methyl, $R^{11}$ is a single bond, phenylene group, —O—$R^{21}$—, or —C(=O)—$Z^1$—$R^{21}$—, $Z^1$ is —O— or —NH—, $R^{21}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety, $Rf^1$ to $Rf^4$ are each independently fluorine, hydrogen or trifluoromethyl, at least one of $Rf^1$ to $Rf^4$ being fluorine, $R^{12}$ to $R^{19}$ are each independently a $C_1$-$C_{12}$ straight, branched or cyclic alkyl group which may contain a carbonyl, ester or ether moiety, $C_6$-$C_{12}$ aryl group, $C_7$-$C_{20}$ aralkyl group, or mercaptophenyl group, $Y^1$ is a single bond or a $C_1$-$C_{12}$ linking group which may contain an ester, ether moiety or lactone ring, $Y^2$ is a single bond, methylene, ethylene, phenylene, fluorinated phenylene, —O—$R^{22}$—, or —C(=O)—$Z^2$—$R^{22}$—, $Z^2$ is —O— or —NH—, $R^{22}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety, and $M^-$ is a non-nucleophilic counter ion.

* * * * *